United States Patent
Liu et al.

(10) Patent No.: US 10,188,743 B2
(45) Date of Patent: Jan. 29, 2019

(54) CYTISINE-LINKED ISOFLAVONOID ANTINEOPLASTIC AGENTS FOR THE TREATMENT OF CANCER

(71) Applicant: UNIVERSITY OF KENTUCKY RESEARCH FOUNDATION, Lexington, KY (US)

(72) Inventors: Chunming Liu, Lexington, KY (US); David S. Watt, Lexington, KY (US); Mykhaylo S. Frasinyuk, Kyiv (UA); Vitaliy M. Sviripa, Lexington, KY (US); Wen Zhang, Lexington, KY (US); Svitlana P. Bondarenko, Kyiv (UA)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/714,647

(22) Filed: Sep. 25, 2017

(65) Prior Publication Data

US 2018/0344862 A1    Dec. 6, 2018

Related U.S. Application Data

(60) Provisional application No. 62/400,333, filed on Sep. 27, 2016.

(51) Int. Cl.
*A61K 31/435* (2006.01)
*A61K 47/54* (2017.01)

(52) U.S. Cl.
CPC ................................ *A61K 47/545* (2017.08)

(58) Field of Classification Search
CPC .................................................. A61K 31/435
See application file for complete search history.

(56) References Cited

U.S. PATENT DOCUMENTS 9,718,799 B2    8/2017    Bondarenko et al.

OTHER PUBLICATIONS

Frasinyuk et al., Organic&Biomolecular Chemistry, 2017, 15, 7623-7629.*
Cancer-1, 2018, https://www.medicalnewstoday.com/articles/320786.php.*
Cancer-2, 2018, https://www.cancer.gov/about-cancer/treatment.*
Bodarenko et al., Chemistry of Natural Compounds, vol. 52, No. 3, 2016, 463-467.*
Bodarenko et al. 2, Chemistry of Natural Compounds, vol. 50, No. 5, 2014, 889-891.*
Bodarenko et al. 3, Chemistry of Natural Compounds, vol. 48, No. 6, 2013, 970-973.*
Bodarenko et al. 4, Chemistry of Natural Compounds, vol. 47, No. 4, 2011, 604-607.*
S. P. Bondarenko et al., "Synthesis of Flavonoid Derivatives of Cytisine. 3. Synthesis of 7-[2-(Cytisin-12-YL)Ethoxy]Isoflavones", Chemistry of Natural Compounds, vol. 48, No. 6, Jan. 2013 [Russian original No. 6, Nov.-Dec. 2012].
S. P. Bondarenko et al., "Synthesis of Cytisine Derivatives of Flavonoids. 2. Aminomethylation of 7-Hydroxyisoflavones", Chemistry of Natural Compounds, vol. 47, No. 4, Sep. 2011 [Russian original No. 4, Jul.-Aug. 2011].
Mykhaylo S. Frasinyuk et al., "Developing antineoplastic agents that target peroxisomal enzymes: cytisine-linked iso? avonoids as inhibitors of hydroxysteroid 17-beta-dehydrogenase-4 (HSD17B4)", The Royal Society of Chemistry, Organic & Biomolecular Chemistry, 2017, No. 15, pp. 7623-7629.
Mykhaylo S. Frasinyuk et al., "Synthesis and tautomerization of hydroxylated isoflavones bearing heterocyclic hemi-aminals", The Royal Society of Chemistry, Organic & Biomolecular Chemistry, 2015, No. 13, pp. 1053-1067.
Mykhaylo S. Frasinyuk et al., "Aminomethylation of Cytisine by 3-Hetaryl-7-Hydroxychromones", Chemistry of Natural Compounds, vol. 43, No. 3, 2007, pp. 285-290.

* cited by examiner

*Primary Examiner* — Sun Jae Yoo
(74) *Attorney, Agent, or Firm* — McDermott Will & Emery LLP

(57) ABSTRACT

Cytisine-linked isoflavonoids, or pharmaceutically acceptable salts thereof or pharmaceutically acceptable compositions thereof, are useful for the treatment of conditions in which cells have a reliance on peroxisomal HSD17B4 to degrade very long chain fatty acids and provide necessary energy for cell proliferation, such as is seen in colorectal cancer and prostate cancer, for example.

8 Claims, 21 Drawing Sheets

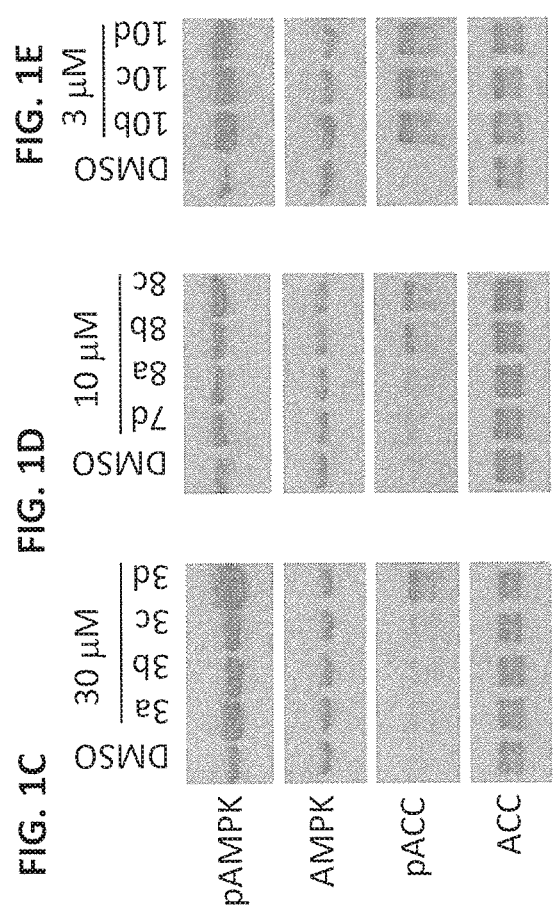

FIG. 3A

| | | | | Dehydrogenase | Hydratase | C-10 binding |
|---|---|---|---|---|---|---|
| HSD17B4 | 1 — Dehydrogenase — 318 — Hydratase — 634 — SCP2L — 736 | | | Yes | Yes | Yes |
| N318 | Dehydrogenase | | | Yes | No | No |
| N634 | Dehydrogenase — Hydratase | | | Yes | Yes | No |
| C919 | Hydratase — SCP2L | | | No | Yes | Yes |

CYTISINE-LINKED ISOFLAVONOID ANTINEOPLASTIC AGENTS FOR THE TREATMENT OF CANCER

CROSS-REFERENCE TO RELATED APPLICATION

This application claims the benefit of U.S. Provisional Application No. 62/400,333 filed 27 Sep. 2016 the entire disclosure of which is hereby incorporated by reference herein.

STATEMENT REGARDING FEDERALLY SPONSORED RESEARCH

This invention was made with government support under Contract Nos. R21 CA139359 and R01 CA172379 awarded by The National Institutes of Health. The Government has certain rights in the invention.

TECHNICAL FIELD

The present disclosure is directed to compounds having antineoplastic activity. In particular, the disclosure is directed to cytisine-linked isoflavonoids and use of such compounds to inhibit cancer cell growth, e.g., prostate or colorectal cancer, in a patient in need thereof.

BACKGROUND

Metabolic dysregulation occurs in many human diseases, including diabetes, cardiovascular diseases and cancer, and raises important questions as to the molecular mechanisms conflating these diseases. Recent reports suggest that metformin, a first-line medication for the treatment of type II diabetes particularly in obese patients, reduces the risk of cancer through its presumed effects on adenosine monophosphate (AMP)-activated protein kinase (AMPK). AMPK plays a central role in maintaining energy homeostasis through its regulation of downstream cellular events including mTOR signaling, lipid catabolism, and glucose metabolism. The precise upstream events connecting metformin to AMPK may involve the serine/threonine kinase LKB1, which is also known as serine/threonine kinase-11 (STK11). In connection with our development of antineoplastic agents, we selected the process of AMPK activation as an initial guide for evaluating new, natural product-derived agents such as semisynthetic isoflavonoids. We utilize the terminology "isoflavones" to describe naturally occurring compounds and "isoflavonoids" to describe compounds with both the naturally occurring pharmacophore and man-made chemical modifications not seen in nature.

SUMMARY OF THE DISCLOSURE

Advantages of the present disclosure include a cytisine-linked isoflavonoid, or pharmaceutically acceptable salt thereof or pharmaceutically acceptable composition thereof, for the treatment of cancer. In particular, the compounds of the present disclosure are useful in treating conditions in which cancer cells, which have a rapacious need for energy, are deprived of a significant energy source, namely the degradation (called beta-oxidation) of very long chain fatty acids. This degradation process proceeds in the peroxisome and requires the enzyme HSD17B4. Inhibition of HSD17B4 in normal cells is not problematic since these cells do not undergo continuous replication at the same rate as cancer cells and hence do not have the same energy demands. HSD17B4 inhibitors are useful agents for the treatment of cancers, such as colorectal cancer and prostate cancer.

These and other advantages are satisfied, at least in part, by a cytisine-linked isoflavonoid compound or method of treating cancer by administering to a patient in need of such treatment an effective amount of a cytisine-linked isoflavonoid compound represented by formula (I):

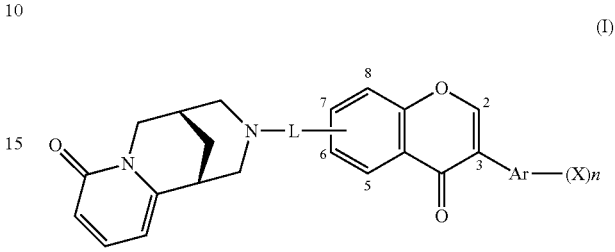

(I)

or pharmaceutically acceptable salt thereof or a pharmaceutical composition thereof. In the cytisine-linked isoflavonoid represented by formula (I), Ar is an aryl or heteroaryl; n is an integer from 1 to 5; each X is independently a halide, or alkoxy, or more than one X on Ar together form a cyclic ether structure; and wherein the compound is substituted on the C-2 position with H, alkyl, cycloalkyl or alkoxy, substituted on the C-5, C-6, C-7, and C-8 positions independently with H, hydroxy (OH), alkyl, cycloalkyl, alkoxy, L is a substituted or unsubstituted di-radical linker group that links the cytisinyl group to either the C-5, C-6, C-7 or C-8 position.

Embodiments include one or more of the following features individually or combined. For example, embodiments of the present disclosure include a cytisinyl-linked isoflavonoid represented by the following formula (II):

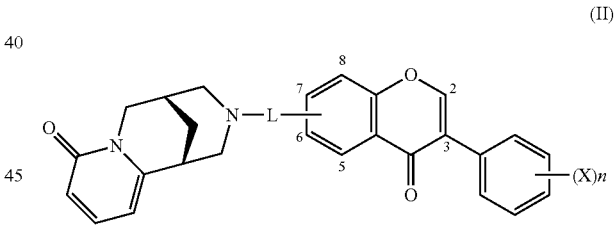

(II)

or pharmaceutically acceptable salt thereof or a pharmaceutical composition thereof, wherein the variables of n, X and L are as defined for formula (I). In this embodiment, L is a substituted or unsubstituted diradical linker group that links the cytisinyl group to the C-7 position in the isoflavonoid. In some embodiments, compounds of formula (I) or (II) or pharmaceutically acceptable salts thereof can include wherein the C-2 substituent is hydrogen H or methyl; n is 1 or 2, X is a halogen or an alkoxy group or two X together form a ring structure; the C-5 substituent is H, hydroxy or alkoxy; the C-6 substitutent is hydrogen H; the C-8 is H, methyl, alkyl or substituted alkyl. Linkers that are useful for the present disclosure include diradicals such as wherein L is a diradical linker group, such as —$R_2$—, —$R_2Z$—$(R'_2)_m$—, —$R_2Z$—$(R'_2)_m$—O—, where m is 0 or 1; $R_2$ and $R'_2$ are independently a $C_{1-8}$ diradical alkyl such as —$(CH_2)_{n1}$— where n1 is 1-8, e.g. 2-8; and Z represents either —$(CH_2)_{n2}$—, —CH(OH)—, —CO—, —C(O)O—, —OC(O)—, or —O—, wherein n2 is 1-4

Another aspect of the present disclosure includes administering to a patient in need of prostate or colorectal cancer treatment an effective amount of at least one compound of formula (I) or (II), or embodiments thereof, or pharmaceutically acceptable salts thereof.

In some embodiments, the administration can include a pharmaceutical composition including an effective amount of at least one compound of formula (I) or (II) or embodiments thereof, or a pharmaceutically acceptable salt thereof, in combination with a pharmaceutically acceptable additive, e.g., a pharmaceutically acceptable carrier or excipient.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIGS. 1A-1H show structures for isoflavonoids and certain effects thereof. In particular, FIG. 1A shows natural isoflavones 1 and 2 and semisynthetic isoflavonoid 3; FIG. 1B shows the synthesis of certain isoflavonoids. (Substituent key: a: R=H and X=H, b: R=H and X=OCH$_3$, c: R=H and X=Cl and d: R=CH$_3$ and X=Cl. Reagent Legend: a, resorcinol, BF$_3$-Et$_2$O; b, DMF, BF$_3$-Et$_2$O, POCl$_3$; c, Ac$_2$O, K$_2$CO$_3$, DMF; d, K$_2$CO$_3$, BrCH$_2$CH$_2$Br; e, piperazine or N-(2-hydroxyethyl)piperazine, NaI, K$_2$CO$_3$, DMF; f, cytisine, NaI, iPr$_2$NH, DMF); FIGS. 1C, 1D and 1E show levels of phosphorylated AMPK and ACC following treatment with isoflavonoids 3, 7, 8 and 10; FIG. 1F shows the effects of cytisine-linked isoflavonoid 10c on AMPK signaling and FIGS. 1G and 1H show three effects of cytisine-linked isoflavonoid 10c on cancer cell proliferation.

FIG. 2A shows the synthesis of a biotinylated, cytisine-linked isoflavonoid 15d. (Reagent Legend: a, MCPBA; b, cytisine, EtOH, 90° C., pressure tube; c, Dess-Martin reagent; d, PEG hydrazide, CeCl$_3$); FIGS. 2B and 2C show levels of phosphorylated AMPK and ACC following treatment with isoflavonoids; FIG. 2D shows purification of binding proteins of isoflavonoids AMPK activator; FIG. 2E shows validation of potential targets by Western blot; FIG. 2F shows HSD17B4 depletion by shRNA activated AMPK; and FIG. 2G shows HSD17B4 depletion by shRNA inhibited LS174T cell proliferation.

FIGS. 3A-3E relate to HSD17B4 protein domains. FIG. 3A is a schematic diagram of HSD17B4 protein domains; FIGS. 3B and 3C show interactions of biotinylated, cytisine-linked isoflavonoid 15d with full-length and truncated HSD17B4; FIG. 3D shows the effects of cytisine-linked isoflavonoid 10c on dehydrogenase activity of HSD17B4; FIG. 3E shows the effects of cytisine-linked isoflavonoid 10c on hydratase activity of HSD17B4.

FIG. 4A shows the effects of cytisine-linked isoflavonoid 10c on fatty acid levels in cancer cells; FIGS. 4B and 4C show the effects of cytisine-linked isoflavonoid 10c on the levels of Acetyl-CoA and ATP in cancer cells; FIGS. 4 D-F show the effects of cytisine-linked isoflavonoid 10c on respiration rates and ATP production in LS174T colon cancer cells.

FIG. 6A shows HSD17B4 depletion by shRNA activated AMPK in PC-3 cells and FIG. 6B shows HSD17B4 depletion by shRNA inhibited PC-3 cell proliferation.

FIG. 7A shows dehydrogenase activities of full-length and truncated HSD17B4 and FIG. 7B shows hydratase activities of full-length and truncated HSD17B4.

DETAILED DESCRIPTION OF THE DISCLOSURE

Figures 1A, 1B:
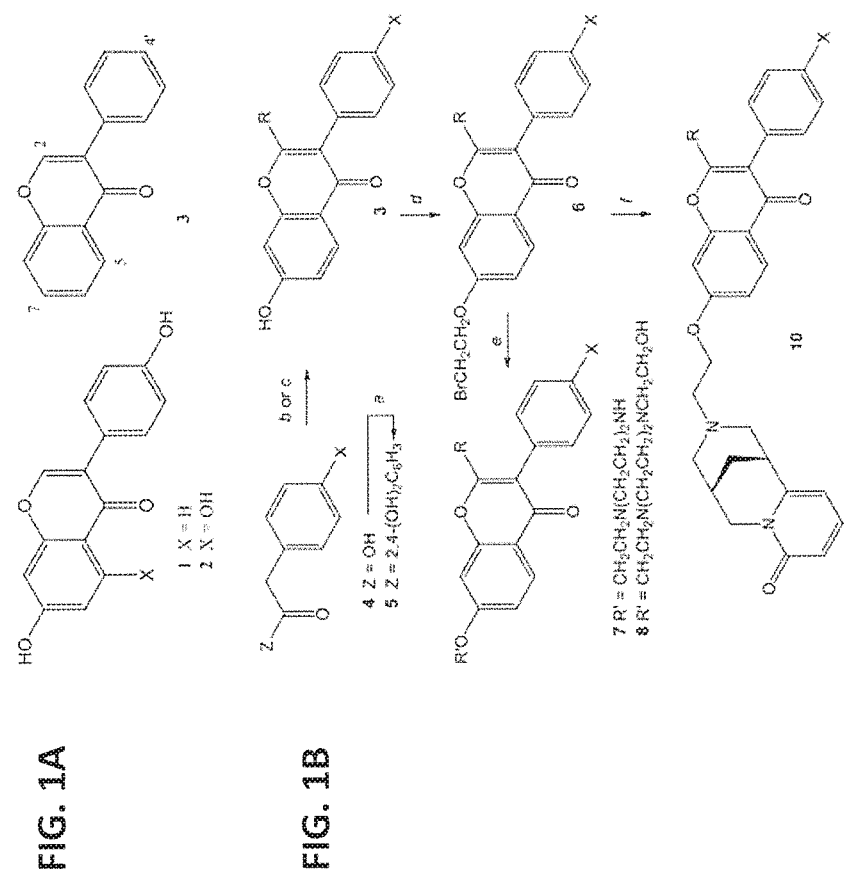

The present disclosure relates to cytisine-linked isoflavonoids, or pharmaceutically acceptable salts or compositions thereof, for use in inhibiting cancer cell growth. The unequivocal and unique biological target of these compounds is an enzyme, hydroxysteroid 17β-dehydrogenase 4 (HSD17B4), in the peroxisome that is responsible for the catabolism (i.e., degradation) of certain lipids. Specifically, this enzyme regulates sterol metabolism and most importantly, the catabolism of very long chain fatty acids (VLCFA). In general, catabolism of fatty acids with 20 or fewer carbons occurs in mitochondria, but these VLCFA (>22 carbons) undergo initial degradation in the peroxisome and the shortened fatty acids then translocate to the mitochondria where their degradation is completed. The cytisine-linked isoflavonoids of the present disclosure selectively block this peroxisomal degradation and deprive cancer cells of the energy source generated by this degradative process that cancer cells need for their unregulated growth.

In addition, it is believed that the cytisine-linked isoflavonoids serve as adenosine monophosphate (AMP)-activated protein kinase (AMPK) activators. AMPK serves as a sensor for maintaining cellular energy homeostasis and undergoes abnormal activation in human diseases such as cancer. The development of direct as well as indirect activators of AMPK represent a means for treating cancer. Hence, the cytisine-linked isoflavonoids of the present disclosure serve as AMPK activators that inhibit lipid catabolism in the peroxisome, disrupt energy homeostasis, and depress cancer cell proliferation. These AMPK activators exert their effect by targeting a peroxisomal, multifunctional enzyme, HSD17B4 and selectively inhibiting the hydratase activity within this multifunctional enzyme. The HSD17B4 inhibitors alter fatty acid profiles, reduce both acetyl CoA levels and ATP/AMP ratios, and activate AMPK when cells are treated with cytisine-linked isoflavonoids in the nanomolar concentration range.

Hence an advantage of the present disclosure includes cytisine-linked isoflavonoids, or pharmaceutically acceptable salts thereof or pharmaceutically acceptable compositions thereof, for the treatment of conditions in which dysfunctional cells have extraordinary energy demands. In the present case where cancer cells require energy derived from the peroxisomal catabolism of very long chain fatty acids, these cytisine-linked isoflavonoids disrupt this energy supply and consequently disrupt cell proliferation. Cytisine-linked isoflavonoids will be useful for treating a variant of cancers including colorectal cancer and prostate cancer In an aspect of the present disclosure, a patient suffering from cancer is treated by administering to such a patient in need of such treatment an effective amount of a cytisinyl-linked isoflavonoid compound, or pharmaceutically acceptable salt thereof or a pharmaceutical composition thereof. The cytisine-linked isoflavonoid compound can be represented by the following formula (I):

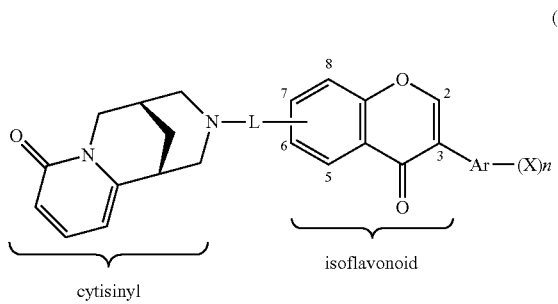

(I)

wherein Ar represents aryl, e.g., phenyl, or heteroaryl, e.g., pyridinyl, diazinyl, pyrimidinyl, oxazolyl or imidazolyl. The variable n represents the number of X groups on Ar and can be an integer from 1 to 5. Each X, e.g., $X^1$, $X^2$, $X^3$, $X^4$, and/or $X^5$, is independently a halide, e.g., a fluoro, chloro, or bromo, or alkoxy (—$OR^1$ where $R^1$ is an alkyl or cycloalkyl, e.g., a $C_{1-8}$ alkyl), or more than one X on Ar together form a cyclic ether structure, e.g., $X^1$ and $X^2$ on Ar together form a —O—R— or —O—R—O— ring, where R is a diradical organo group. Examples of such groups include a methylenedioxy, dimethylenedioxy, etc. The isoflavonoid moiety can be substituted at each of its C-2, C-5, C-6, C-7, C-8 positions, provided at least one of C-5, C-6, C-7 or C-8 is bonded to L. In certain embodiments, the cytisinyl moiety is linked to the isoflavonoid by linker L at the C-7 position. The substituent on C-2, C-5, C-6, C-7, C-8 can independently be the same or different and include hydrogen (H); hydroxy (OH); alkyl or cycloalkyl; e.g., methyl, ethyl, cyclopropyl; alkoxy (—$OR^1$) an —$OCOR^1$ group such —$OCOCH_3$. L is a substituted or unsubstituted diradical group that links the cytisinyl moiety to the isoflavonoid moiety at the C-7 position. Linkers that are useful for the present disclosure include diradicals such as wherein L is a diradical linker group, such as —$R_2$—, —$R_2Z$— $(R'_2)_m$—, —$R_2Z$—$(R'_2)_m$—O—, where m is 0 or 1; $R_2$ and $R'_2$ are independently a $C_{1-8}$ diradical alkyl such as —$(CH_2)_{n1}$— where n1 is 1-8, e.g. 2-8; and Z represents either —$(CH_2)_{n2}$—, —CH(OH)—, —CO—, —C(O)O—, —OC(O)—, or —O—, wherein n2 is 1-4. In an embodiment of the present disclosure, L is —$(CH_2)_{n1}(CH_2)_{n2}$O—, —$(CH_2)_{n1}$CH(OH)$(CH_2)_{n1}$O—, and —$(CH_2)_{n1}$CO $(CH_2)_{n1}$O—.

Embodiments of the present disclosure include a cytisine-linked isoflavonoid, or pharmaceutically acceptable salt thereof or a pharmaceutical composition thereof, represented by the following formula (II)

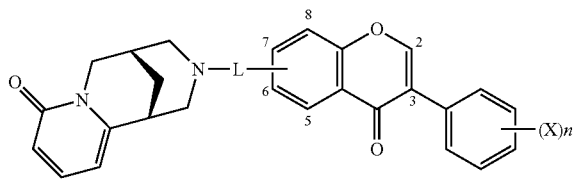

(II)

wherein the variables of n, X and L are as defined for formula (I). In this embodiment, L is a substituted or unsubstituted diradical linker group that links the cytisinyl group to the C-7 position in the isoflavonoid. In some embodiments, compounds of formula (I) or (II) or pharmaceutically acceptable salts thereof, the isoflavonoids possess a hydrogen or $CH_3$ group at C-2; the isoflavonoids possess a phenyl group at C-3 in which X is a fluoro, chloro, bromo or alkoxy group (—$OR^1$ where $R^1$ is an alkyl or cycloalkyl, e.g., a $C_{1-8}$ alkyl), or more than one X on Ar together form a cyclic ether structure, e.g., $X^1$ and $X^2$ on Ar together form a —O—R— or —O—R—O— ring, where R is a diradical organo group); the isoflavonoids possess hydrogen H; hydroxy (OH); alkyl or cycloalkyl; e.g., methyl, ethyl, cyclopropyl; alkoxy (—$OR^1$) an —$OCOR^1$ group such —$OCOCH_3$ at C-5, C-6 and C-8; and the isoflavonoids possess a hydroxy group (OH) at C-7 that is alkylated by the linker L, which is a substituted or unsubstituted diradical group that links the cytisinyl moiety to the isoflavonoid moiety.

While it may be possible for compounds of the present disclosure to be administered without an additive, it is preferable to present them as a pharmaceutical composition. According to a further aspect, the present disclosure provides a pharmaceutical composition comprising a compound or mixture of compounds of Formula (I) and/or Formula (II) or a pharmaceutically acceptable salt, solvate, or hydrate thereof, together with one or more pharmaceutically acceptable additives, e.g., a pharmaceutically acceptable carrier or excipient and optionally one or more other therapeutic ingredients. The additive(s) must be "acceptable" in the sense of being compatible with the other ingredients of the formulation and not deleterious to the recipient thereof. The term "pharmaceutically acceptable carrier" includes vehicles and diluents.

The compounds and/or compositions of the present disclosure are useful for treating animals, and in particular, mammals, including humans, as patients. Thus, humans and other animals, and in particular, mammals, suffering from hyperproliferative disorders such as cancer, can be treated by administering to the patient an effective amount of one or more of the cytisinyl-linked isoflavonoids according to the present disclosure, or a pharmaceutically acceptable salt thereof, optionally in a pharmaceutically acceptable additive, either alone, or in combination with other known pharmaceutical agents. Treatment according to the present disclosure can also be by administration of the compounds and/or compositions of the present disclosure in conjunction with other conventional cancer therapies, such as radiation treatment or surgery or administration of other anti-cancer agents.

In the course of developing the cytisine-linked isoflavonoids of the present disclosure and identifying their mechanisms of HSD17B4 inhibition and concomitant AMPK activation, we screened a library of semisynthetic isoflavonoids that possess the pharmacophore found in these natural products but that also possess structural modifications not seen in nature. The rationale behind the selection of isoflavonoids for this screening program rested on isoflavones, such as daidzein (1) and genistein (2) (FIG. 1A), that appear in dietary supplements with alleged health benefits including claims for the treatment of cancer. We synthesized and screened semisynthetic isoflavonoids and identified a specific subgroup of cytisine-linked isoflavones as potent AMPK activators with a unique cancer-relevant, peroxisomal enzymatic target, namely HSD17B4.

Structure-activity studies focused on modifications at C-2, C-7 and the C-4', which is the para-position in the isoflavonoid scaffold 3. Synthesis of these isoflavonoids 3 required the condensation of resorcinol with arylacetic or heteroarylacetic acids 4 to furnish the deoxybenzoins 5, and the subsequent condensation of 5 with either N,N-dimethylformamide and boron trifluoride etherate or with acetic anhydride and potassium carbonate to afford the isoflavonoids 3 (FIG. 1B). Preliminary screening identified the most promising isoflavonoids 3 as those with hydrogen or methyl groups at C-2, para-chlorophenyl groups at C-3, and hydroxyl groups at C-7. Most isoflavonoids exhibited AMPK activation only at relatively high 30 μM concentrations (representative sample in FIG. 1C). Isoflavonoids 3c and 3d were the most active AMPK activators and displayed, as expected, modest activation of acetyl CoA carboxylase that lay downstream of AMPK.

Additional modifications that improved potency in AMPK activation included the attachment of various ω-aminoalkyl groups to the C-7 hydroxyl group in 3 through spacers of various carbon-chain lengths. The alkylation, for example, of the isoflavonoids 3 with 1,2-dibromoethane secured the 7-(2-bromoethoxy)isoflavonoids 6, and the subsequent condensation of 6 with either piperazine or N-(2-hydroxyethyl)piperazine led to the (piperazin-1-yl)ethoxy)-substituted isoflavonoids 7 and 8, respectively (FIG. 1B). These piperazine-substituted isoflavonoids 7 and 8 activated AMPK at lower concentrations (i.e., 10 μM) than those at which the unmodified isoflavonoids 3 (FIG. 1D versus 1C) were active. In addition to screening similarly substituted isoflavonoids bearing other monocyclic, heterocyclic amines (data not shown), we examined naturally occurring alkaloids as potential partners for the N-alkylation of 7-(2-bromoethoxy)isoflavonoids 6. In particular, the covalent coupling of 6 with cytisine (9) led to the 7-(2-cytisinylethoxy)isoflavonoids 10 that displayed potent AMPK activation in the low μM range (FIG. 1E). Thus, through a logical series of SAR studies, we arrived at the potent cytisine-linked isoflavonoids.

Figure 1F:
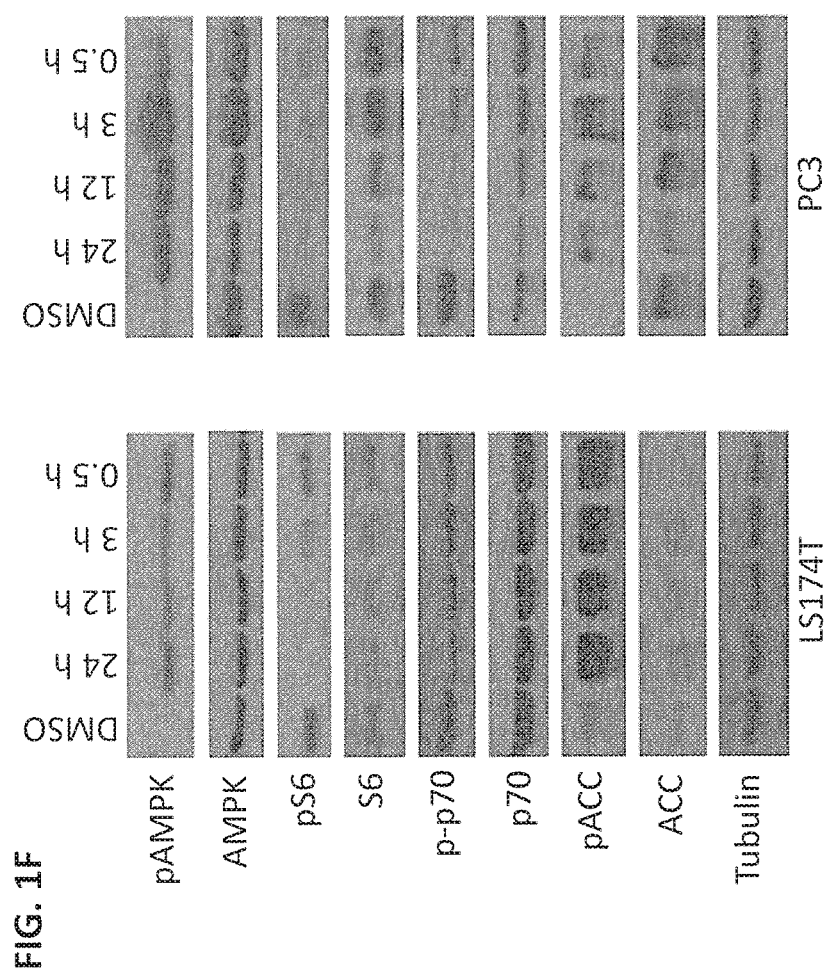
Figure 1H:
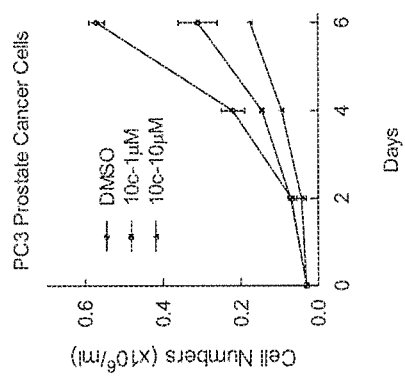
Figure 1G:
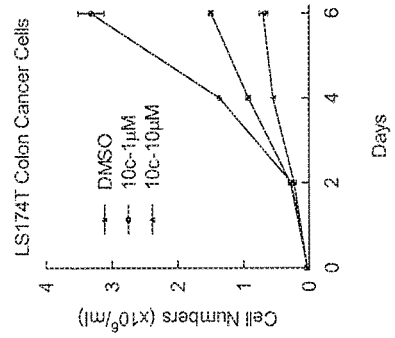

We next tested the activity of these potent cytisine-linked isoflavonoids such as 10c (FIG. 1B in which the letter c designates the following substitution pattern: R=H and X=Cl) on the proliferation of cancer cells. We treated PC-3 prostate cancer cells and LS174T colon cancer cells with 10c and analyzed a panel of markers by Western blotting (FIG. 1F). Treatment with 10c activated AMPK in both cell lines, and induced appreciable ACC phosphorylation, a key regulator in lipid biosynthesis downregulated during rapid growth. In addition, treatment with 10c also inhibited the phosphorylation of p70 and S6, key components of the mTor pathway important for cell growth. As a result, the cystisine-linked isoflavonoid 10c significantly inhibited the proliferation of both PC-3 and LS174T cells (FIGS. 1G and 1H).

Figure 2C:
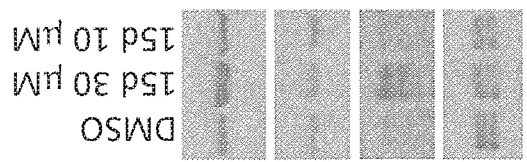
FIGS. 2A-2G show structures for cytisine-linked isoflavonoid and certain results thereof. In particular.
Figure 2B:
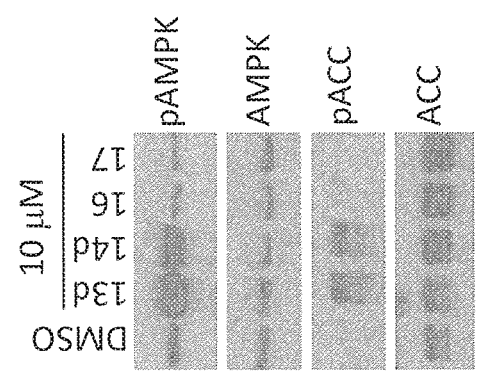
Figure 2A:
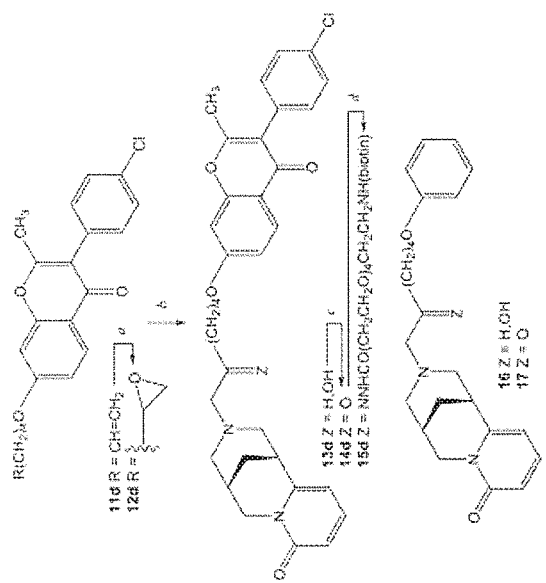

To identify the molecular target, we sought a biotinylated analog of this cytisine-linked isoflavonoid 10c that retained biological activity as an AMPK activator and that positioned the biotin moiety sufficiently far from the isoflavonoid to permit capture by steptavidin. Balancing these requirements led us to synthesize a biotinylated analog with a longer linker L than the two carbons found in 10c in order to provide adequate separation between the streptavidin-biotin complex and the complex between 10c and its target. In addition, we needed a functional "handle" on this longer linker for the attachment of the biotin tag. After some experimentation to find the appropriate combination of linker length and covalent attachment site, we found that the alkylation of the isoflavonoid 3d with 6-bromo-1-hexene furnished the 5-hexenyloxyisoflavonoid (11d), and treatment of 11d with meta-chloroperoxybenzoic acid led to the epoxide 12d (FIG. 2A). Alkylation of 12d with cytisine (9) gave the intermediate alcohol 13d; oxidation with Dess-Martin's reagent secured the ketone 14d; and condensation with a PEG biotinylated hydrazide afforded the cytisinyl-linked isoflavonoid 15d. The intermediate alcohol 13d and the ketone 14d as well as the biotinylated cytisinyl-linked isoflavonoid 15d activated AMPK (FIGS. 2B and 2C) in the 10-30 μM range, which was sufficient to proceed with a pull-down assay. As controls to establish the requirement for both the cytisine and isoflavone moieties for AMPK activation, we also synthesized the cytisinyl-substituted alcohol 16 and ketone 17 (FIG. 2A) in which a phenoxy group replaced the isoflavonoid, and we established that 16 and 17 were inactive as AMPK activators (FIG. 2B).

Figure 2D:
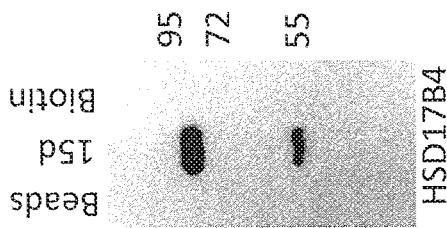

Identification of the direct target of these AMPK activators involved incubation of 15d with LS174T cell lysates and a subsequent pull-down assay using biotinylated 15d bound to streptavidin beads. The binding proteins were eluted with 2.5 mM biotin and analyzed by 4-12% SDS-PAGE gel using colloidal blue staining (FIG. 2D). We identified two specific bands (F1 and F2) in the 15d-containing sample compared with the control samples containing only beads or only beads and biotin. These two bands were excised from gels and analyzed by NanoLC-ESI-MS/MS. The band F1 (FIG. 2D) contained two proteins: [1] peroxisomal hydroxysteroid 17-dehydrogenase-4 (HSD17B4); and [2] mitochondrial methylcrotonoyl-CoA carboxylase subunit alpha (MCCA). The band F2 also matched HSD17B4.

Figure 2E:
Figure 2E:
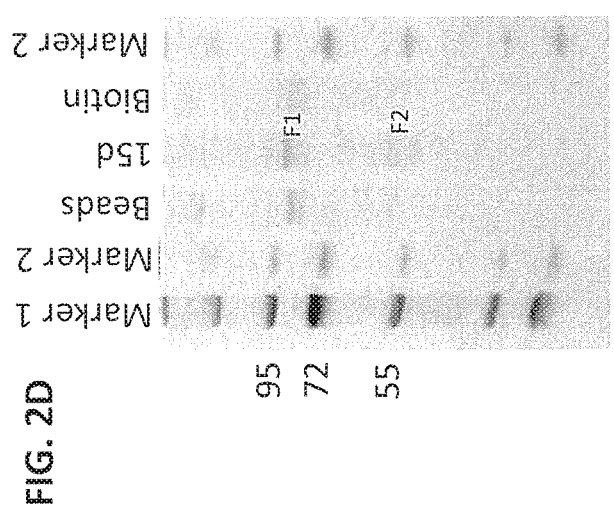

We validated these results by Western blotting using antibodies against HSD17B4 and MCCA. We discounted the MCCA protein, which appeared in both 15d-containing sample and in the control sample, as a non-specific binding protein of the stepavidin complex with 15d. We focused on the multifunctional HSD17B4 protein, which appeared only in the 15d-containing sample (FIG. 2E), as a specific binding protein of the biotinylated, cytisine-linked isoflavonoid 15d in the peroxisome. The multifunctional nature of HSD17B4 included two of the four enzymatic activities required for the beta-oxidation of very long-chain fatty acids (VLCFA) in the peroxisome. Proteolytic cleavage of HSD17B4 generated a N-terminal 32-kD fragment possessing α,β-dehydrogenase activity and a C-terminal 45-kD fragment with hydratase activity as well as a solute-carrier-protein-2-like domain (SCP2L). The HSD17B4 antibody (GeneTex) recognized the full-length and the C-terminal fragment (FIG. 2E).

Figure 2G:
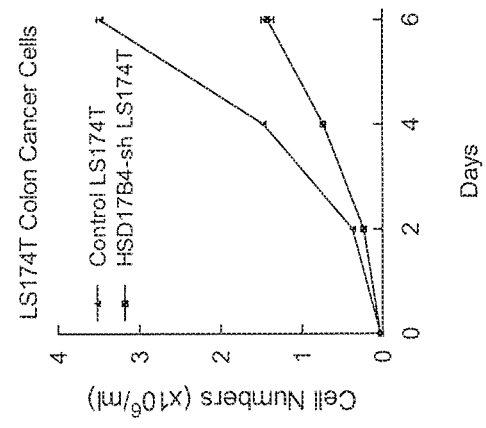
Figure 2F:
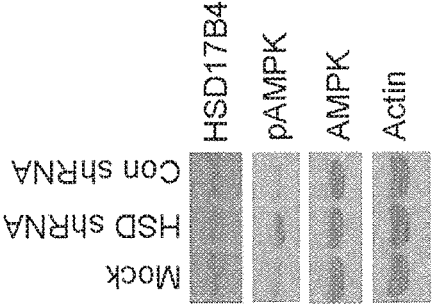
Figure 6A:
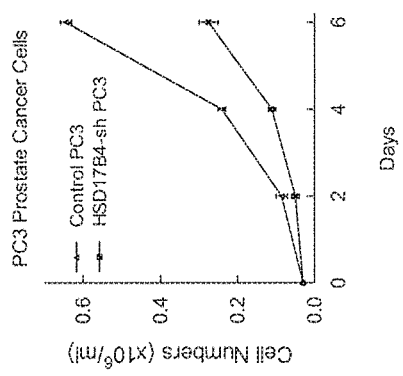
FIGS. 6A-6B relate to HSD17B4 depletion.
Figure 6B:
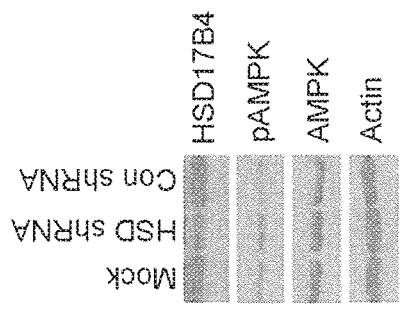

We presumed that disruption of VLCFA processing in the peroxisome by inhibitors of HSD17B4 affected energy homeostasis, particularly in cancer cells, and triggered AMPK phosphorylation. To validate HSD17B4 as a direct target of these isoflavonoid inhibitors leading to AMPK activation, we knocked down HSD17B4 using shRNA in LS174T colon cancer cells and PC-3 prostate cancer cells. As expected, HSD17B4 depletion increased AMPK phosphorylation (FIGS. 2F and 6A). Depletion of HSD17B4 also significantly inhibited the proliferation of both LS174T and PC-3 cells (FIGS. 2G and 6B). These results were consistent with results seen in the treatment of these same cells either with 10c (FIGS. 1F-H) or with 13d, 14d or 15d (FIGS. 2B-C) and these results suggested that these cytisine-linked isoflavonoids activated AMPK by directly targeting HSD17B4.

Figure 3B:
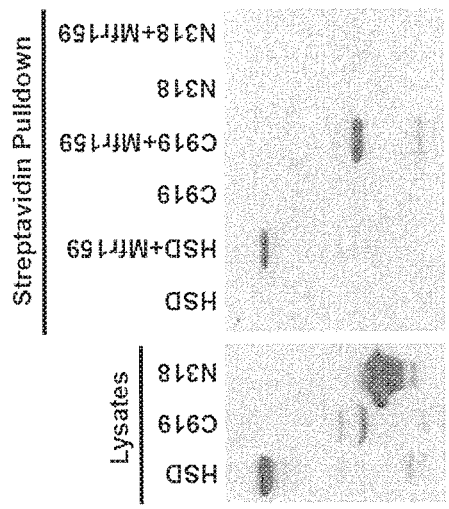
Figure 3C:
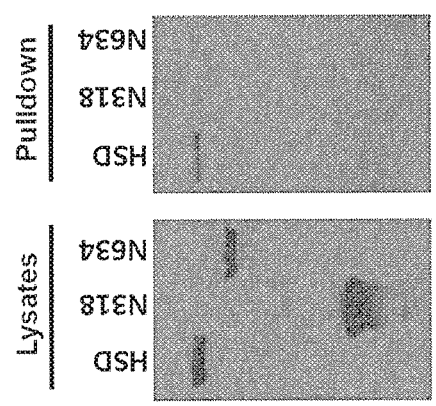

We next sought to delineate if these cystisine-linked isoflavonoid inhibitors were selective for one of the two enzymatic activities, either the α,β-dehydrogenase or hydratase activity, found in HSD17B4. We generated a panel of truncated HSD17B4 constructs and purified these truncated proteins as well as the full-length protein from E. coli (FIG. 3A). We evaluated the binding of 15d to these constructs using the streptavidin bead-based pull-down assay. The full-length HSD17B4, but not the C-terminus-truncated fragments N318 and N634, interacted with 15d (FIG. 3B). However, the N-terminus-truncated fragment C919 also strongly bound 15d (FIG. 3C), which suggested that the isoflavonoids bound to the C-terminus of HSD17B4 and inhibited selectively the hydratase activity of HSD17B4.

Figure 3E:
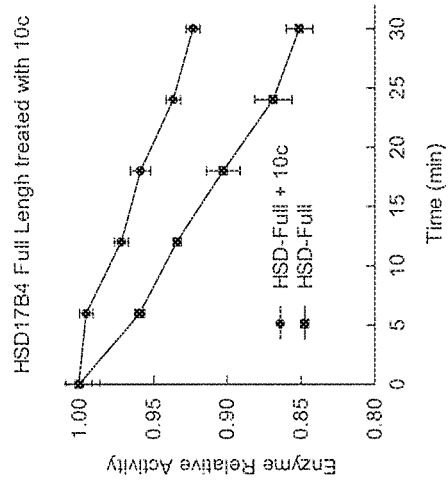
Figure 3D:
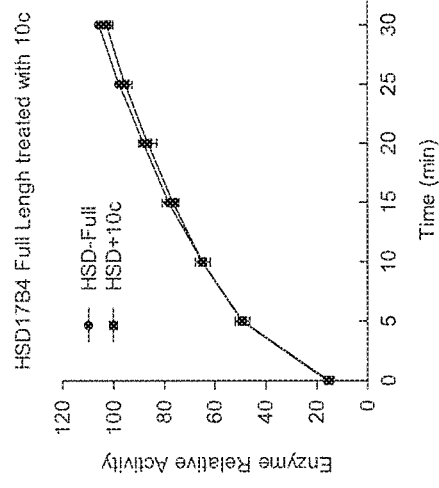
Figure 7B:
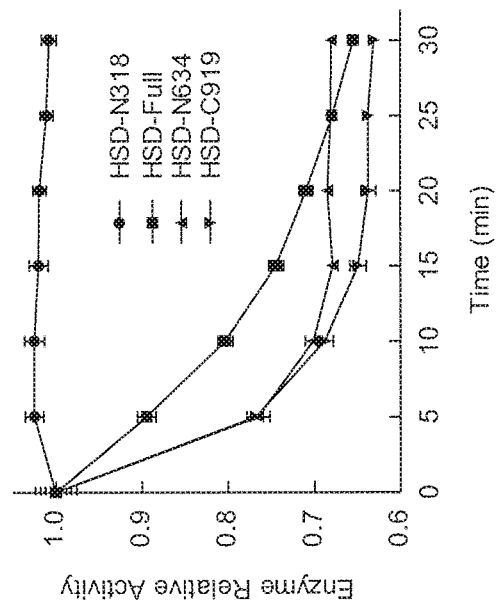
FIGS. 7A-7B show certain activity.
Figure 7A:
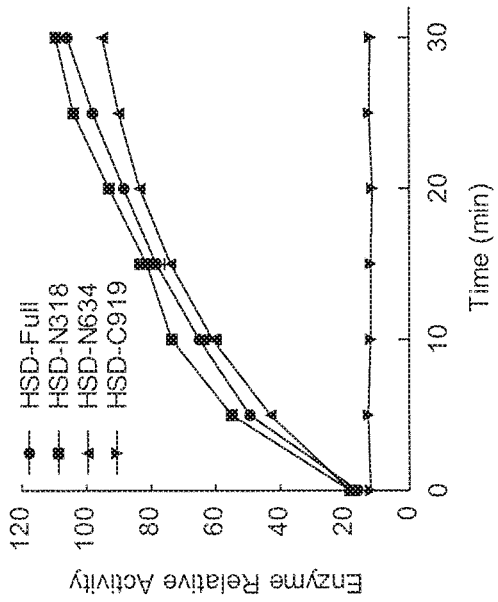

We acquired further evidence along these lines through studies using the N-terminal α,β-dehydrogenase and C-terminal hydratase fragments of HSD17B4 as well as the full-length protein. We evaluated the α,β-dehydrogenase activity using DL-3-hydroxylbutyryl-CoA as a substrate and the conversion of $NAD^+$ to NADH as a readout. We concomitantly measured the hydratase activity using crotonoyl-CoA as a substrate and the diminished ultraviolet absorption of the α,β-unsaturated thioester chromophore as readout. The full-length protein, as expected, had both enzyme activities (FIGS. 7A and 7B). The C-terminal-truncated fragments N318 and N634 but not the N-terminal-truncation fragment C919 had α,β-dehydrogenase activity (FIG. 7A). The C-terminal fragment N634 and the N-terminal fragment C919, but not the C-terminal fragment N318, had hydratase activity (FIG. 7B), as summarized in FIG. 3A. These results were consistent with previous reports about the interlocking roles of the different domains in HSD17B4. We tested the effects of cytisine-linked isoflavonoid 10c on each enzyme activity and found that 10c had no effect on the α,β-dehydrogenase activity (FIG. 3D) but significantly inhibited the hydratase activity (FIG. 3E). In summary, cytisine-linked isoflavonoids specifically bound the C-terminus of HSD17B4 and selectively inhibited the hydratase activity of this multifunctional HSD17B4 enzyme.

Figure 4A:
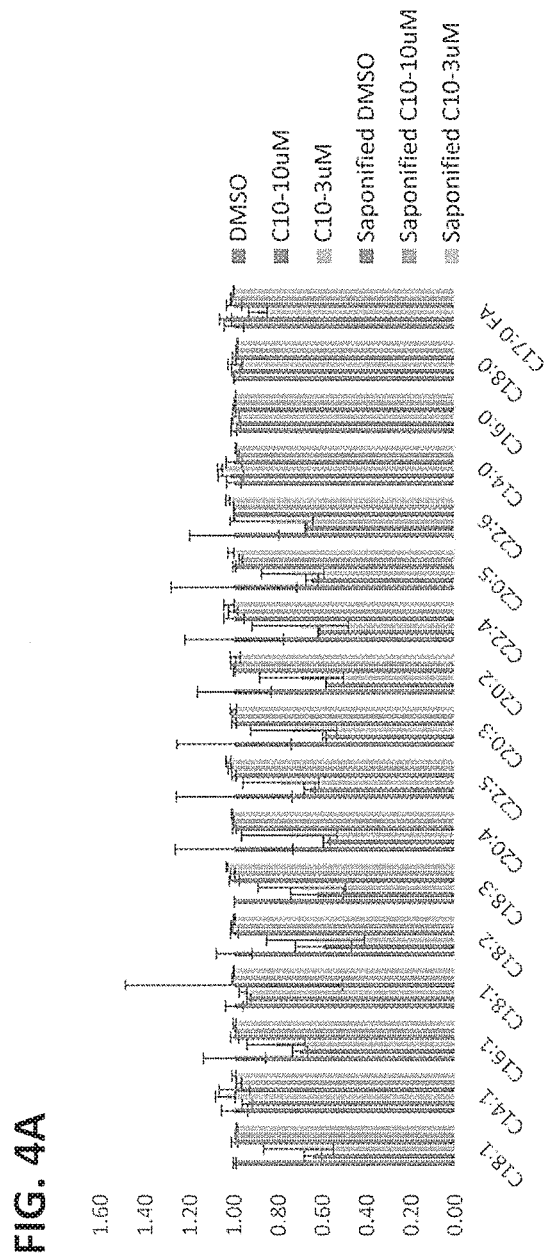
FIGS. 4A-4F relate to fatty acid levels in cancer cells. In particular.
Figures 4B, 4C:
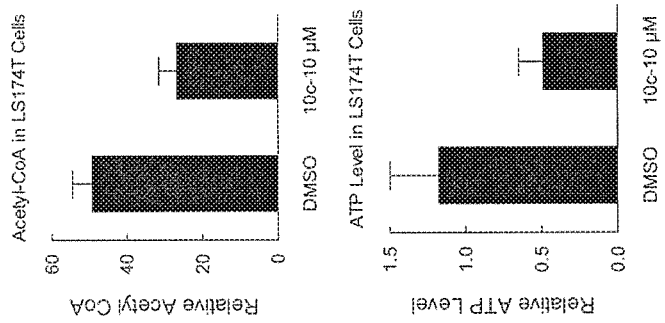

To test the effects of these HSD17B4 inhibitors on lipid metabolism, we analyzed the fatty acid profiles of LS174T colon cancer cells after treatment with cytisine-linked isoflavonoid 10c, although we recognized that fatty acid catabolism occurred in interdependent processes in two different organelles at different rates. Reflective of this complexity, we found that cytisine-linked isoflavonoid 10c reduced the levels of a number of fatty acids (FIG. 4A), not just the long-chain fatty acids. Collectively, this outcome suggested that these cytisine-linked isoflavonoids activated AMPK through their effects on the hydratase activity in HSD17B4 and broad effects on fatty acid catabolism involved a combination of diminished acetyl CoA levels arising out of VLCFA and energy homeostasis in cancer cells. Consistent with this hypothesis, treatment with cytisine-linked isoflavonoid 10c decreased the levels of both acetyl CoA and ATP (FIGS. 4B and 4C) in LS174T cancer cells. We assumed that inhibition of HSD17B4 affected VLCFA and depressed the levels of certain long-chain fatty acids destined for the mitochondria. As a consequence, the rate of mitochondrial beta-oxidation increased, and as we observed, the level of all fatty acids, not just the VLCFA, was decreased.

Figure 4D:
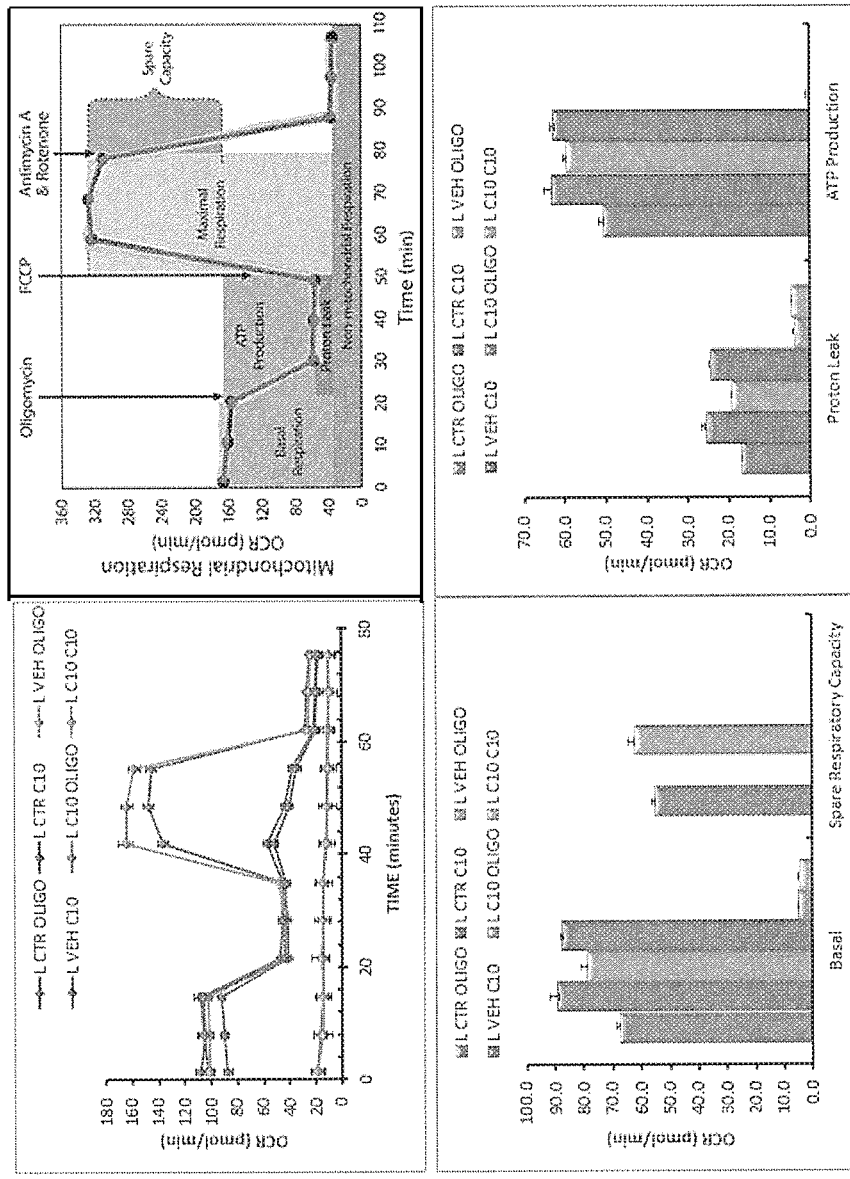
Figure 4E:
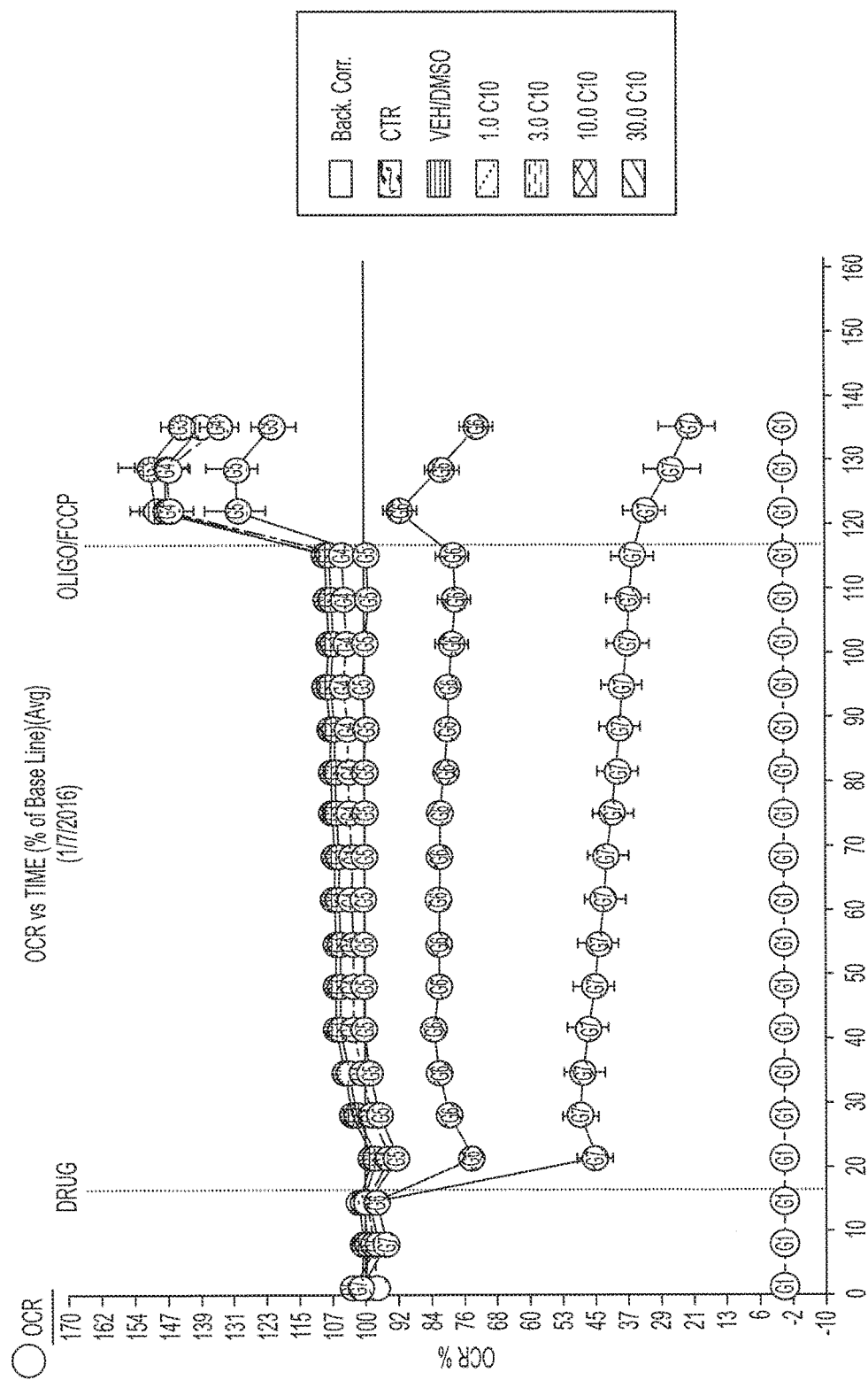
Figure 4F:
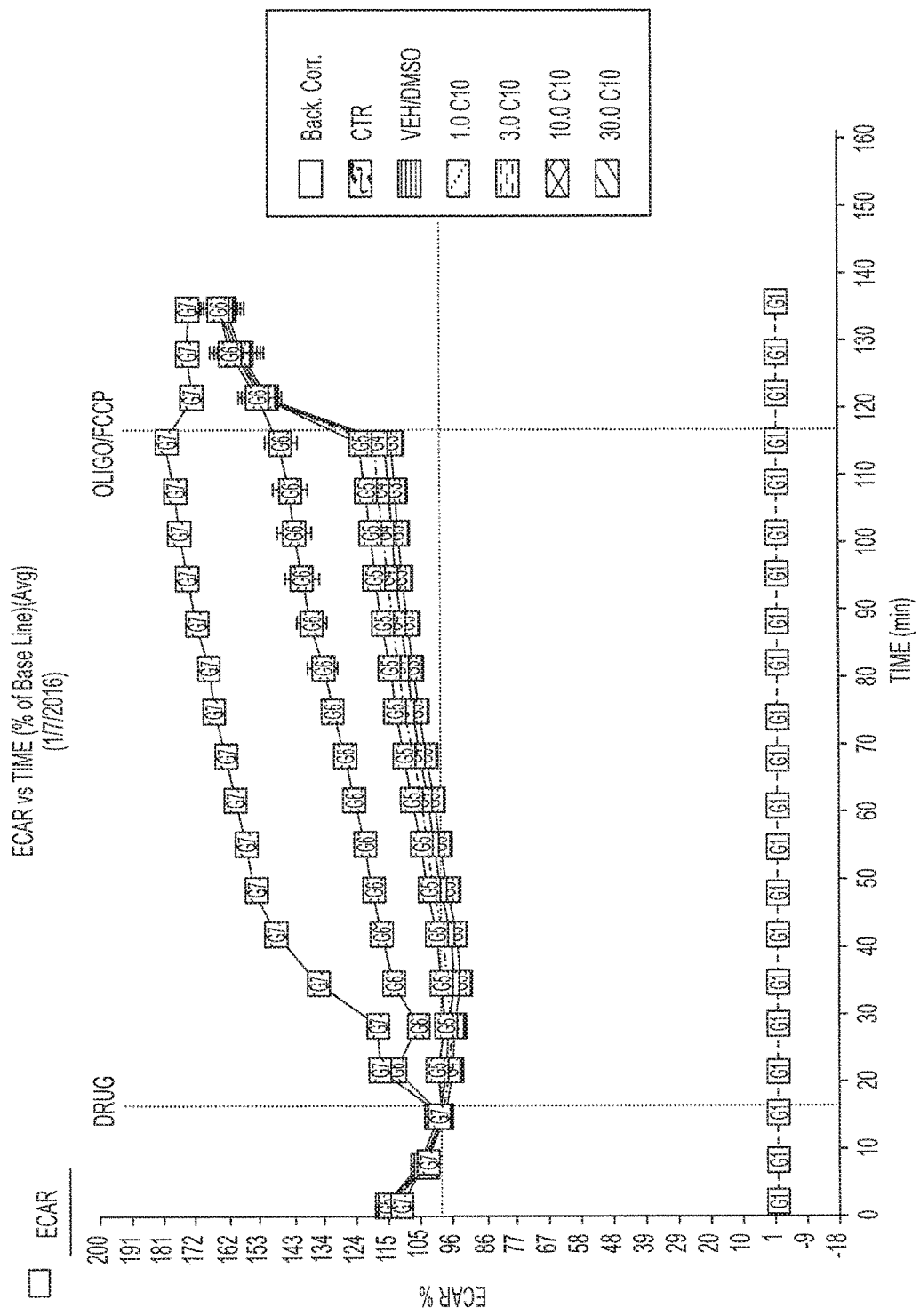
Figure 5:
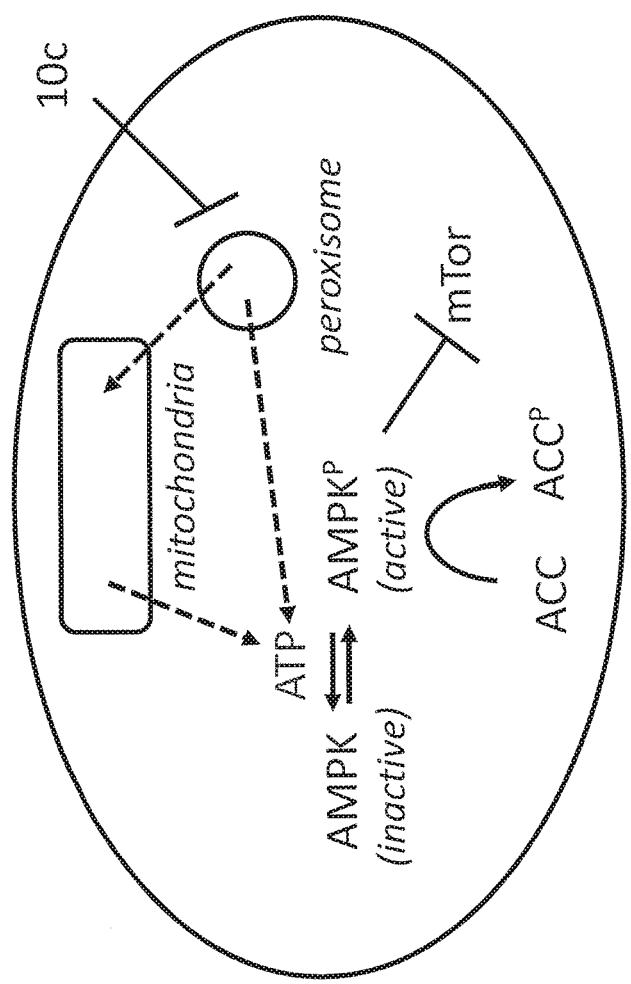
FIG. 5 is a schematic showing disruption of ATP production from mitochondria or peroxisomes leading to increased levels of phosphorylated AMPK, which inhibits ACC-mediated lipogenesis and mTor-mediated cancer cell proliferation.
Figure 8:
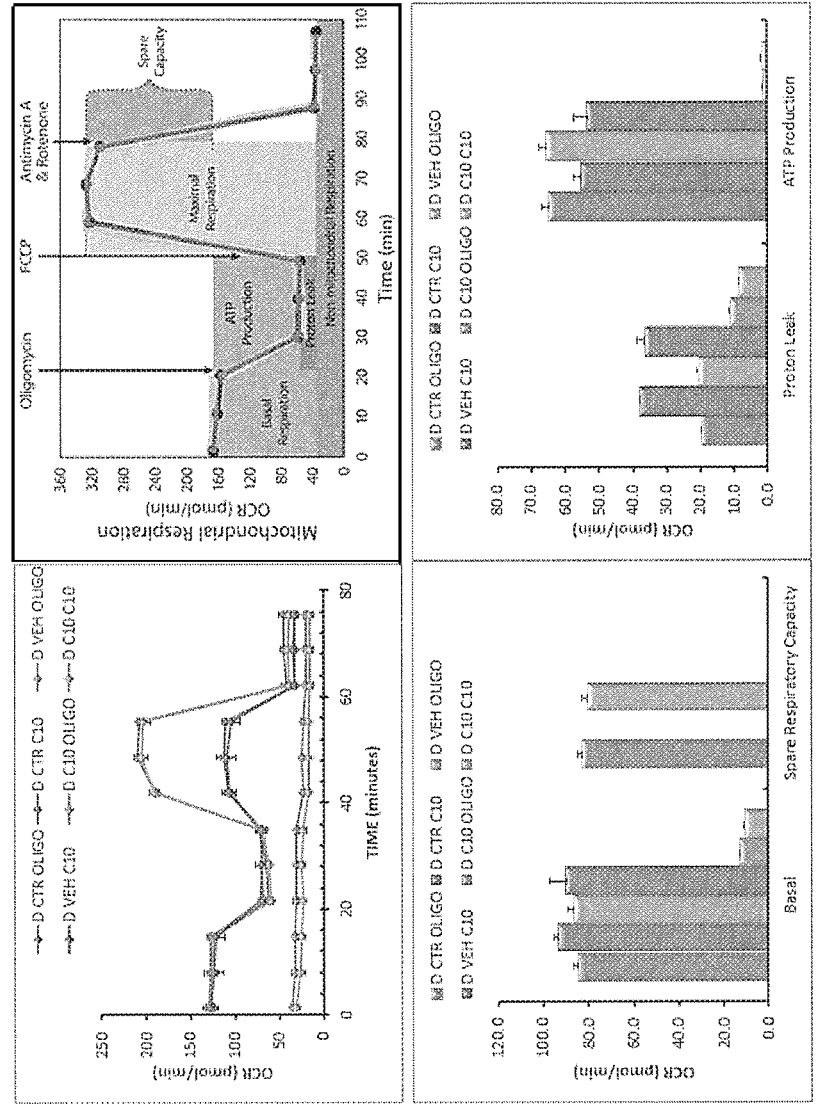
FIG. 8 shows cytisine-linked isoflavonoid 10c reduced respiration rate and ATP production of DLD1 colon cancer cells.
Figure 9A:
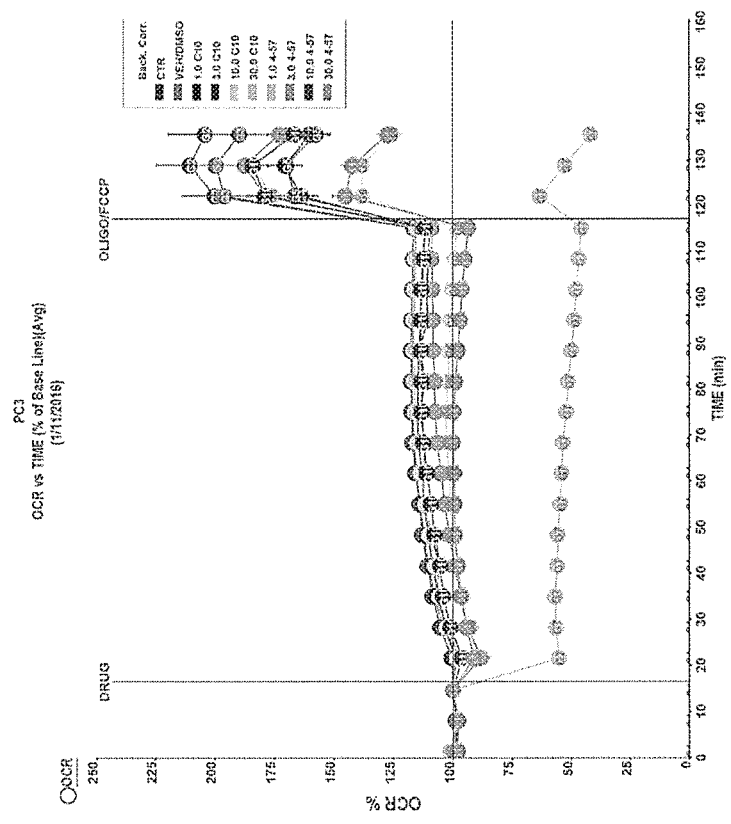
FIGS. 9A and 9B show cytisine-linked isoflavonoid 10c inhibited respiration reduced respiration rate of PC-3 prostate cancer cells.
Figure 9B:
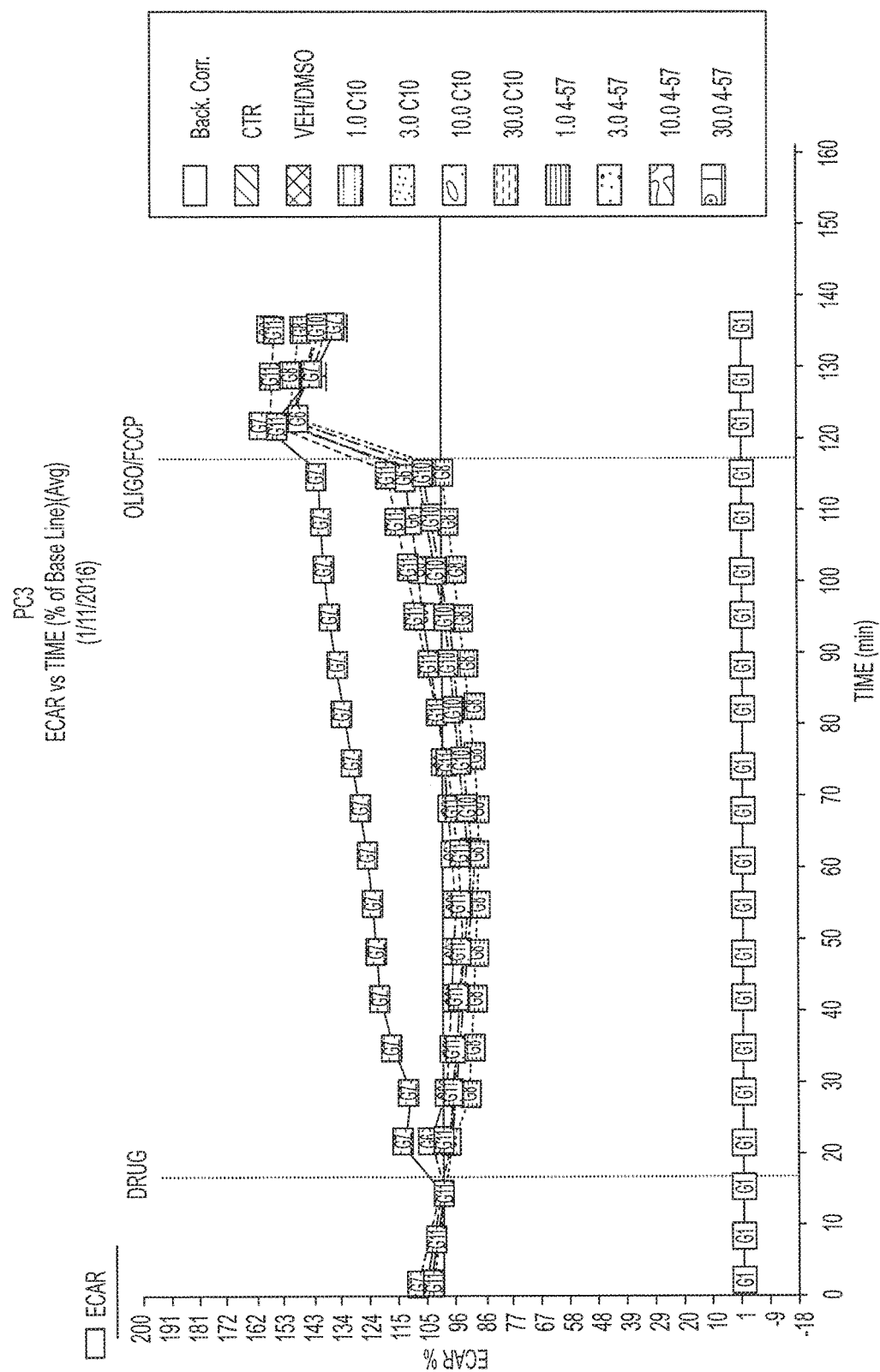

We further characterized the effects of cytisine-linked isoflavonoid 10c on energy metabolism using a Seahorse XF assay (FIG. 4D-F) that measured oxygen consumption rate (OCR), which was an indicator of mitochondrial respiration, and measured extracellular acidification rate (ECAR), which was largely the result of glycolysis. We found that cytisine-linked isoflavonoid 10c significantly reduced the respiration rates of LS174T cells and reduced the levels of ATP production in both respirometry (OCR) and extracellular acidification rate (ECAR) assays. Similar results were found in DLD-1 colon cancer cells and PC-3 prostate cancer cells (FIGS. 8 and 9). These OCR findings were consistent with the prior evaluation of these cytisine-linked isoflavonoids that targeted the hydratase activity in HSD17B4, inhibited VLCFA beta-oxidation, depressed acetyl CoA generation, decreased the ratio of ATP/AMP, and triggered AMPK activation (FIG. 5).

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Materials and Characterization. Chemicals were purchased from Sigma Aldrich (Milwaukee, Wis.) or Fisher Scientific (Pittsburgh, Pa.) or were synthesized according to literature procedures. Hydrazide-$PEG_4$-biotin was purchased from Thermo Fisher Scientific (Florence, Ky.). Solvents were used from commercial vendors without further purification unless otherwise noted. Nuclear magnetic resonance spectra were determined on a Varian instrument ($^1$H, 400 MHz; $^{13}$C, 100 Mz). High resolution electrospray ionization (ESI) mass spectra were recorded on a Thermo-Scientific Q Exactive Orbitrap mass spectrometer. Resolution was set at 100,000 (at 400 m/z). Samples were introduced through direct infusion using a syringe pump with a flow rate of 5 μL/min. Purity of compounds was greater than 95% as established using combustion analyses determined by Atlantic Microlabs, Inc. (Norcross, Ga.). Compounds were chromatographed on preparative layer Merck silica gel F254 unless otherwise indicated. Methods for the synthesis of isoflavonoids were described in the Supplemental Material section.

Cell Culture. LS74T colon cancer cells were cultured in MEM/EBSS (Hyclone SH30024) and PC-3 prostate cancer cells were cultured in DMEM/F-12 HAM Mixture (Sigma D8437) containing 10% Fetal Bovine Serum (Atlanta Biological S11150). Cells ($3.5 \times 10^4$ cells per well) were split into 12-well plates. After 24 h, 10 μM of each compound were added to each well. DMSO was used as a control. Each experiment was done in triplicate. Cell viability and number were analyzed using the Vi-Cell XR Cell Viability Analyzer (Beckman Coulter). To knock-down HSD17B4 levels, PC-3 and LS174 cell lines were infected with lenti-virus carrying pLKO.1-control shRNA and pLKO.1-HSD17B4b shRNA, respectively. Control shRNA and HSD17B4b shRNA cloned in pLKO.1 vectors with puromycin-resistance selection marker were purchased from Sigma. Lentiviral stocks were prepared as previously described (Yu, 2012).

Biochemistry. Western blotting: Cells were lysed in the appropriate volume of lysis buffer (50 mM HEPES, 100 mM NaCl, 2 mM EDTA, 1% glycerol, 50 mM NaF, 1 mM Na3VO4, 1% Triton X-100, with protease inhibitors). The following antibodies were used: HSD17B4 (GeneTex, GTX103864), AMPK (Cell Signaling, 2532), pAMPK (Cell Signaling, 2535), ACC (Cell Signaling, 3676), pACC (Cell Signaling, 11818), $p^{70}$ (Cell Signaling, 2708), p-$p^{70}$ (Cell Signaling, 9914), S6 (Cell Signaling, 2217), pS6 (Cell Signaling, 4858), MCCA (GeneTex, GTX110062), tubulin (Hybridoma Bank, E7), Actin (Sigma, A1978), His-tag (BD Pharmingen, 552564).

Streptavidin-agarose pulldown: Biotinylated compound 15d (FIG. 2A) was incubated with cell lysates and streptavidin beads. The binding proteins were pulled down and analyzed by 4-12% SDS-PAGE as described previously. The protein bands were identified by NanoLC-ESI-MS/MS at ProtTech Inc. For binding and enzymatic assays, His-tagged HSD17B4 constructs were clone and truncated by PCR using pET28. The full-length and truncated proteins were purified from bacteria BL21.

The enzymatic activities of HSD17B4 were analyzed using the method reported by Novikov et al. (J. Biol. Chem., 1994, 269, 27125). Dehydrogenase assay: The purified HSD17B4 enzyme was diluted in 200 μL reaction buffer (60 mM Hydrazine, pH 8.0; 1 mM $NAD^+$; 50 mM KCl; 0.01% Triton-X100 and 0.05% BSA) and incubated with 25 μM substrate, DL-β-hydroxybutyryl CoA lithium salt (Sigma H0261). The reaction was quantified by measuring the fluorescent product NADH (excitation: 340 nm; emission 460 nm). Hydratase assay: The purified HSD17B4 enzyme was diluted in 200 μL reaction buffer (0.32 M Tris-HCl, pH7.4; 5.9 mM EDTA, 0.006% BSA) and incubated with 0.2 mM substrate, crotonoyl CoA (Sigma 28007). The reaction was quantified by measuring the remaining substrate using absorbance at 280 nm.

Cell Metabolism. Acetyl-CoA analysis: Cells grown in 6 cm plates were treated with DMSO or inhibitors, and harvested in lysis buffer (20 mM Tris pH 7.5, 150 mM NaCl, 1 mM EDTA, 1 mM EGTA, 1% Triton X-100, 2.5 mM sodium pyrophosphate, 1 mM $Na_3VO_4$, 1 ug/mL Leupeptin, 1 mM PMSF and 1:100 Protease inhibitor cocktail). Supernatants were analyzed using PicoProbe Acetyl CoA kit (Abcam, ab87546).

ATP analysis: Cells growing in 12-well plates were treated with DMSO or inhibitors, and lysed by adding 1 mL boiling D.D. water. Supernatants were analyzed by luminescence using ATP Determination Kit (Invitrogen, A22066).

Seahorse assay: $3 \times 10^4$ cells were seeded in XF96 Cell Culture microplate (80 μL of $3.75 \times 10^5$ cells/m:). On the next day, cells were treated with DMSO or inhibitors and analyzed using the Seahorse analyzer in Redox Metabolism Shared Resource Facility (RM SRF) at the Markey Cancer Center.

Fatty acid analysis: Free and total fatty acids (after saponification) were prepared as reported previously (Spencer et al. *Diabetes* 62(5):1709-1717) converted to N-(4-aminomethylphenyl)pyridinium derivatives (Bollinger et al. *J Lipid Res* 54(12):3523-3530) and quantitated HPLC electrospray ionization tandem mass spectrometry with quantitation accomplished using exogenously added heptadecanoic acid as a recovery standard and reference to offline calibrations generated using authentic fatty acid standards.

The following cytisine-linked isoflavonoid compounds were tested for AMPK activation.

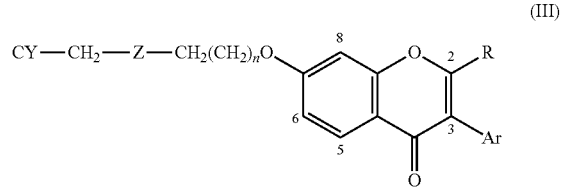

(III)

| Compound | Ar | R | n | Z | CY | AMPK-fold Activation (10 μM) |
|---|---|---|---|---|---|---|
| 10a | $C_6H_4$-4-Cl | H | 0 | $CH_2$ | 12-cytisinyl | 3.6 |
| 10b | $C_6H_4$-4-Cl | $CH_3$ | 0 | $CH_2$ | 12-cytisinyl | 9.9 |
| 10c | $C_6H_4$-4-Cl | $CH_3$ | 1 | $CH_2$ | 12-cytisinyl | 4.1 |
| 10d | $C_6H_4$-4-Cl | H | 1 | CH(OH) | 12-cytisinyl | 2.2 |
| 10e | $C_6H_4$-4-Cl | $CH_3$ | 1 | CH(OH) | 12-cytisinyl | 1.3 |
| 10f | $C_6H_4$-4-Cl | $CH_3$ | 1 | C=O | 12-cytisinyl | N/A |
| 10g | $C_6H_4$-4-Cl | $CH_3$ | 2 | CH(OH) | 12-cytisinyl | 3.2 |
| 10h | $C_6H_4$-4-Cl | $CH_3$ | 3 | CH(OH) | 12-cytisinyl | 2.9 |
| 10i | $C_6H_4$-4-Cl | $CH_3$ | 3 | C=O | 12-cytisinyl | N/A |
| 10j | $C_6H_4$-4-Cl | $CH_3$ | 4 | CH(OH) | 12-cytisinyl | 3.2 |
| 10k | $C_6H_4$-4-Cl | $CH_3$ | 4 | C=O | 12-cytisinyl | 1.1 (at 3 μM) |
| 10l | $C_6H_5$ | H | 0 | $CH_2$ | 12-cytisinyl | 2 |
| 10m | $C_6H_5$ | $CH_3$ | 0 | $CH_2$ | 12-cytisinyl | 3.4 |
| 10n | $C_6H_4$-4-Br | H | 0 | $CH_2$ | 12-cytisinyl | 8.4 |
| 10o | $C_6H_4$-4-Br | $CH_3$ | 0 | $CH_2$ | 12-cytisinyl | 5.9 |
| 10p | $C_6H_4$-4-OMe | H | 0 | $CH_2$ | 12-cytisinyl | 6 |
| 10q | $C_6H_4$-4-OMe | $CH_3$ | 0 | $CH_2$ | 12-cytisinyl | 4.2 |
| 10r | $C_6H_3$-3,4-$(OMe)_2$ | H | 0 | $CH_2$ | 12-cytisinyl | 2.4 |
| 10s | $C_6H_3$-3,4-$(OMe)_2$ | $CH_3$ | 0 | $CH_2$ | 12-cytisinyl | 4.9 |

Preparation of Cytisine-Linked Isoflavonoids.

Materials and Characterization. Chemicals were purchased from Sigma Aldrich (Milwaukee, Wis.) or Fisher Scientific (Pittsburgh, Pa.) or were synthesized according to literature procedures. Hydrazide-$PEG_4$-biotin was purchased from Thermo Fisher Scientific (Florence, Ky.). Solvents were used from commercial vendors without further purification unless otherwise noted. Nuclear magnetic resonance spectra were determined on a Varian instrument (1H, 400 MHz; 13C, 100 Mz). High resolution mass spectra (HRMS) were recorded on a Thermo Scientific Q Exactive Orbitrap mass spectrometer. Resolution was set at 140,000. Samples were introduced through direct infusion using a syringe pump with a flow rate of 5 μL/min. Purity of compounds was greater than 95% as established using combustion analyses determined by Atlantic Microlabs, Inc. (Norcross, Ga.). Compounds were chromatographed on preparative layer Merck silica gel F254 unless otherwise indicated.

General Procedure for the Synthesis of Isoflavones 3.

To a solution of deoxybenzoin (10 mmol) in DMF (7 mL) at 30-40° C. under an argon atmosphere was added dropwise 3.7 mL of a 98% solution of boron trifluoride etherate. The mixture was stirred for 30 min, and phosphorous oxytrichloride (2 mL, 21.5 mmol) was added. The mixture was heated at 60° C. for 3-5 h, cooled, poured into water and extracted with ethyl acetate. The organic solution was dried over anhydrous $MgSO_4$. The product was isolated by crystallization (from either methanol or ethanol) to afford isoflavones 3.

7-Hydroxy-3-phenyl-4H-chromen-4-one (3a)

Yield: 69%; mp 209-210° C. (lit[1] mp 210-213° C.). $^1$H NMR (400 MHz, DMSO-$d_6$) δ 10.86 (s, 1H), 8.41 (s, 1H), 8 (d, 1H, J=8.8 Hz), 7.62-7.55 (m, 2H), 7.5-7.36 (m, 3H), 6.97 (dd, 1H, J=8.8, 2 Hz), 6.9 (d, 1H, J=2 Hz); $^{13}$C NMR (100 MHz, DMSO-$d_6$) δ 174.4, 162.7, 157.5, 153.9, 132.1, 129, 128.1, 127.7, 127.3, 123.6, 116.6, 115.3, 102.2. NMR data was consistent with reported data.

7-Hydroxy-3-(4-methoxyphenyl)-4H-chromen-4-one (3b)

Yield: 53%; mp 259-260° C. (lit[9] mp 259-261° C.). $^1$H NMR (400 MHz, DMSO-$d_6$) δ 10.8 (s, 1H), 8.34 (1H), 7.97 (d, 1H, J=8.7), 7.51 (d, 2H, J=8.8 Hz), 6.99 (d, 2H, J=8.8 Hz), 6.94 (dd, 1H, J=8.7, 2.3 Hz), 6.87 (d, 1H, J=2.3 Hz), 3.78 (s, 3H); $^{13}$C NMR (100 MHz, DMSO-$d_6$) δ 174.6, 162.6, 158.9, 157.4, 153.2, 130.1, 127.3, 124.2, 123.2, 116.6, 115.2, 113.6, 102.1, 55.2. NMR data was consistent with reported data.

3-(4-Chlorophenyl)-7-hydroxy-4H-chromen-4-one (3c)

Yield: 59%; mp 260-261° C. (lit[14] mp 260° C.); $^1$H NMR (400 MHz, DMSO-$d_6$) δ 10.86 (s, 1H), 8.45 (s, 1H), 7.98 (d, 1H, J=8.8 Hz), 7.61 (d, 2H, J=8.4 Hz), 7.5 (d, 2H, J=8.4 Hz), 6.96 (dd, 1H, J=8.8, 2.4 Hz), 6.89 (d, 1H, J=2.4 Hz); $^{13}$C NMR (100 MHz, DMSO-$d_6$) δ 174.2, 162.8, 157.5, 154.1, 132.5, 131, 130.7, 128.1, 127.3, 122.3, 116.5, 115.4, 102.2. NMR data was consistent with reported data.

3-(4-Chlorophenyl)-7-hydroxy-2-methyl-4H-chromen-4-one (3d)

Acetic anhydride (3 mL, 31.7 mmol) was added to a suspension of potassium carbonate (94.2 g, 30.4 mmol) and α-4-chlorophenyl-2,4-dihydroxyacetophenone (2 g, 7.6 mmol) in DMF (20 mL) and the resulting suspension was heated at 120° C. for 8 h under an argon atmosphere. The mixture was cooled and poured into water (100 mL). The precipitate was filtered, washed with water (two 100 mL portions) and diethyl ether (100 mL) to afford 1.91 g (88%) of the product as a white solid: mp 277-278° C.; $^1$H NMR (400 MHz, DMSO-$d_6$) δ 10.88 (s, 1H), 7.87 (d, 1H, J=8.6 Hz), 7.48 (d, 2H, J=8.4 Hz), 7.3 (d, 2H, J=8.4 Hz), 6.9 (dd, 1H, J=8.6, 2 Hz), 6.83 (d, 1H, J=2 Hz), 2.24 (s, 3H); $^{13}$C NMR (100 MHz, DMSO-$d_6$) δ 174.6, 162.8, 162.6, 157.1, 132.5, 132.3, 132.2, 128.1, 127.1, 121, 115.4, 114.9, 101.9, 19.2. HRMS (ESI) Calcd for $C_{16}H_{12}O_3Cl$: 287.0480 $(M+H)^+$. Found 287.0471. Anal. Calcd for $C_{16}H_{11}O_3Cl$: C, 67.03; H, 3.87. Found: C, 66.87; H, 4.04.

General Procedure of for the Synthesis Deoxybenzoins 5.

To a mixture of resorcinol (60 mmol) and phenylacetic acid (60 mmol) under an argon atmosphere was added 74 mL of 98% solution of boron trifluoride etherate. The mixture was heated to 85° C. for 3-5 h. The mixture was poured into cold water and extracted with ethyl acetate. The combined organic layers were washed with brine and dried over anhydrous $MgSO_4$. The product was purified by column chromatography (using 1:20 to 1:3 ethyl acetate-hexanes or using 1:99 to 2:98 methanol-dichloromethane) to afford deoxybenzoins 5.

1-(2,4-dihydroxyphenyl)-2-phenylethanone (5a)

Yield: 60%; mp 111-112° C. (lit[4] mp 110-113° C.); $^1$H NMR (400 MHz, CDCl$_3$) δ 12.69 (s, 1H), 7.75 (d, 1H, J=8.6 Hz), 7.37-7.32 (m, 2H), 7.3-7.24 (m, 3H), 6.4-6.34 (m, 2H), 5.76 (s, 1H), 4.21 (s, 2H); $^{13}$C NMR (100 MHz, CDCl$_3$) δ 202.4, 165.7, 162.9, 134.4, 133, 129.5, 128.9, 127.3, 113.7, 108.2, 103.8, 45. NMR data was consistent with reported data in DMSO-$d_6$.

1-(2,4-Dihydroxyphenyl)-2-(4-methoxyphenyl)ethanone (5b)

Yield: 63%; mp 154-155° C. (lit[4] mp 156-157° C.); $^1$H NMR (400 MHz, DMSO-$d_6$) δ 12.56 (s, 1H), 10.66 (s, 1H), 7.94 (d, 1H, J=9 Hz), 7.2 (d, 2H, J=8.8 Hz), 6.87 (d, 2H, J=8.8 Hz), 6.39 (dd, 1H, J=9, 2.3 Hz), 6.25 (d, 1H, J=2.3 Hz), 4.2 (s, 2H), 3.72 (s, 3H); $^{13}$C NMR (100 MHz, DMSO-$d_6$) δ 202.5, 164.9, 164.7, 158, 133.6, 130.5, 127, 113.8, 112.1, 108.2, 102.5, 55, 43.2. NMR data was consistent with reported data in DMSO-$d_6$.

α-4-Chlorophenyl-2,4-dihydroxyacetophenone (5c)

Yield: 49%; mp 157-158° C. (lit[4] mp 150-150.5° C.); $^1$H NMR (400 MHz, DMSO-$d_6$) δ 12.41 (s, 1H), 10.71 (s, 1H), 7.93 (d, 1H, J=9 Hz), 7.37 (d, 2H, J=8.2 Hz), 7.29 (d, 2H, J=8.2 Hz), 6.41 (dd, 1H, J=9, 1.6 Hz), 6.26 (d, 1H, J=1.6 Hz), 4.33 (s, 2H); $^{13}$C NMR (100 MHz, DMSO-$d_6$) δ 201.6, 165, 164.5, 134.2, 133.5, 131.6, 131.4, 128.3, 112.3, 108.3, 102.5, 43.4. NMR data was consistent with reported data in acetone-$d_{65}$ and methanol-$d_{46}$.

General Procedure for 7-(2-bromoethoxy)isoflavones 6

To a solution of 2 mmol of 7-hydroxyisoflavone 3 in DMF (10 mL) was added $K_2CO_3$ (690 mg, 5 mmol) and 1,2-dibromoethane (0.9 mL, 10.4 mmol). The mixture was stirred for 3 h at 80° C. under a nitrogen atmosphere. The product was cooled and poured into cold water. The precipitate was filtered, washed successively with water and cold diethyl ether to afford 7-(2-bromoethoxy)isoflavones 6.

7-(2-Bromoethoxy)-3-phenyl-4H-chromen-4-one (6a)

Yield: 77%; mp 200-201° C. (lit[13] mp 202-204° C.); $^1$H NMR (400 MHz, CDCl$_3$) δ 8.24 (d, 1H, J=8.8 Hz), 7.95 (s, 1H), 7.56 (d, 2H, J=7.2 Hz), 7.48-7.34 (m, 3H), 7.02 (dd, 1H, J=8.8, 2 Hz), 6.88 (d, 1H, J=2 Hz), 4.4 (t, 2H, J=6.1 Hz), 3.7 (t, 1H, J=6.1 Hz); $^{13}$C NMR (100 MHz, CDCl$_3$) δ 175.7, 162.5, 157.9, 152.8, 132, 129.1, 128.6, 128.3 (128.31), 128.3 (128.27), 125.5, 119.1, 114.8, 101.3, 68.3, 28.4. NMR data was consistent with reported data in DMSO-d$_6$.

7-(2-Bromoethoxy)-3-(4-methoxyphenyl)-4H-chromen-4-one (6b)

Yield: 80%. mp 174-175° C. (lit$^{12}$ mp 181.5-182.5° C.); $^1$H NMR (400 MHz, DMSO-d$_6$) δ 8.44 (s, 1H), 8.05 (d, 1H, J=8.8 Hz), 7.53 (d, 2H, J=8.6 Hz), 7.22 (d, 1H, J=2.4 Hz), 7.12 (dd, 1H, J=8.8, 2.4 Hz), 7 (d, 2H, J=8.6 Hz), 4.5 (t, 2H, J=5.2 Hz), 3.87 (t, 2H, J=5.2 Hz), 3.79 (s, 3H); $^1$H NMR (400 MHz, CDCl$_3$) δ 8.23 (d, 1H, J=9 Hz), 7.93 (s, 1H), 7.5 (d, 2H, J=8.8 Hz), 7.01 (dd, 1H, J=9, 2.4 Hz), 6.97 (d, 2H, J=8.8 Hz), 6.86 (d, 1H, J=2.4 Hz), 4.4 (t, 2H, J=6.4 Hz), 3.84 (s, 3H), 3.7 (t, 2H, J=6.4 Hz); $^{13}$C NMR (100 MHz, CDCl$_3$) δ 175.9, 162.4, 159.7, 157.9, 152.2, 130.2, 128.2, 125.1, 124.2, 119, 114.7, 114.1, 101.2, 68.3, 55.5, 28.5. NMR data was consistent with reported data in CDCl$_3$.

7-(2-Bromoethyloxy)-3-(4-chlorophenyl)chromen-4-one (6c)

Yield: 85%; mp 188-189° C.; $^1$H NMR (400 MHz, DMSO-d$_6$) δ 8.54 (s, 1H), 8.06 (d, 1H, J=9 Hz), 7.64 (d, 2H, J=8.4 Hz), 7.51 (d, 2H, J=8.4 Hz), 7.25 (d, 1H, J=2.4 Hz), 7.14 (dd, 1H, J=9; 2.4 Hz), 4.51 (t, 2H, J=5.3 Hz), 3.87 (t, 2H, J=5.3 Hz); $^1$H NMR (400 MHz, CDCl$_3$) δ 8.23 (d, 1H, J=9.2 Hz), 7.95 (s, 1H), 7.51 (d, 2H, J=8.4 Hz), 7.41 (d, 2H, J=8.4 Hz), 7.03 (dd, 1H, J=9.2, 2.4 Hz), 6.88 (d, 1H, J=2.4 Hz), 4.4 (t, 2H, J=6.3 Hz), 3.7 (t, 2H, J=6.3 Hz); $^{13}$C NMR (100 MHz, CDCl$_3$) δ 175.4, 162.6, 157.9, 152.8, 134.3, 130.4, 130.3, 128.8, 128.2, 124.5, 118.9, 114.9, 101.3, 68.4, 28.4. HRMS (ESI) Calcd for C$_{17}$H$_{13}$O$_3$Br$^{37}$Cl: 380.9713 (M+H)$^+$. Found: 380.9711. Anal. Calcd for C$_{17}$H$_{12}$O$_3$BrCl: C, 53.79; H, 3.19. Found: C, 54.09; H, 3.27.

7-(2-Bromoethoxy)-3-(4-chlorophenyl)-2-methyl-4H-chromen-4-one (6d)

To a solution of 7-hydroxyisoflavone 3d (573 mg, 2 mmol) in anhydrous DMF (10 mL) was added K$_2$CO$_3$ (690 mg, 5 mmol) and 1,2-dibromoethane (0.9 mL, 10.4 mmol). The mixture was stirred at 80° C. for 3 h under a nitrogen atmosphere. The mixture was filtered, and DMF was evaporated. The product was isolated by column chromatography using ethyl acetate-hexanes (from 1:9 to 3:7) to give 485 mg (62%) of 6d: mp 160-161° C. (lit$^{12}$ mp 165-167° C.); $^1$H NMR (400 MHz, DMSO-d$_6$) δ 7.95 (d, 1H, J=8.6 Hz), 7.5 (d, 2H, J=8.4 Hz), 7.33 (d, 2H, J=8.4 Hz), 7.21 (d, 1H, J=2.4 Hz), 7.09 (dd, 1H, J=8.6; 2.4 Hz), 4.5 (t, 2H, J=5.5 Hz), 3.87 (t, 2H, J=5.5 Hz), 2.27 (s, 3H); $^{13}$C NMR (100 MHz, DMSO-d$_6$) δ 174.6, 163.2, 162.3, 157, 132.5, 132.3, 132, 128.1, 126.9, 121.3, 116.7, 114.8, 101.2, 68.5, 31, 19.2. NMR data was consistent with reported data in CDCl$_{3 12}$. Anal. Calcd for C$_{18}$H$_{14}$O$_3$BrCl: C, 54.92; H, 3.58. Found: C, 54.85; H, 3.48.

General Procedure for the Synthesis of Piperazinyl Isoflavones 7 and 8.

A mixture of 1 mmole of isoflavone 6, either piperazine or 1-(2-hydroxyethyl)piperazine (1.2 mmol), NaI (1 mmol) and diisopropylethylamine (0.6 mL, 3.5 mmol) in DMF (9 mL) was stirred for 3 h at 60° C. under a nitrogen atmosphere. The mixture was cooled; the solvent was evaporated; and the product was purified by column chromatography using methanol-dichloromethane (1:9 to 1:3) to afford piperazinyl-substituted isoflavones 7 or 8 as white solids.

3-(4-Chlorophenyl)-7-(2-(piperazin-1-yl)ethoxy)-4H-chromen-4-one (7c)

To a solution of 378 mg (1 mmole) of 6c in DMF (10 mL) was added piperazine (172 mg, 2 mmol), NaI (150 mg, 1 mmol). and K$_2$CO$_3$ (276 mg, 2 mmol). The mixture was stirred for 2 h at 60° C. under a nitrogen atmosphere. The mixture was cooled and poured into cold water (100 mL). The precipitated was collected and washed with cold water. The product was recrystallized from methanol to afford 306 mg (79%) of 7c as a white solid: mp 147-148° C.; $^1$H NMR (400 MHz, CDCl$_3$) 8.19 (d, 1H, J=9 Hz), 7.94 (s, 1H), 7.5 (d, 2H, J=8.6 Hz), 7.4 (d, 2H, J=8.6 Hz), 7 (dd, 1H, J=9, 2.4 Hz), 6.86 (d, 1H, J=2.4 Hz), 4.2 (t, 2H, J=5.7 Hz), 2.96-2.9 (m, 4H), 2.87 (t, 2H, J=5.7 Hz), 2.64-2.53 (m, 4H); $^{13}$C NMR (100 MHz, CDCl$_3$) δ 175.5, 163.4, 158, 152.7, 134.3, 130.5, 130.4, 128.8, 127.9, 124.4, 118.5, 115.2, 101, 66.7, 57.6, 54.9, 46.1. HRMS (ESI) Calcd for C$_{21}$H$_{22}$O$_3$N$_2$Cl: 385.1324 (M+H)+. Found 385.1327. Rapid air oxidation precluded obtaining a satisfactory combustion analysis.

7-(2-(4-(2-Hydroxyethyl)piperazin-1-yl)ethoxy)-3-phenyl-4H-chromen-4-one (8a)

Yield: 60%; mp 159-160° C.; $^1$H NMR (400 MHz, CDCl$_3$) δ 8.21 (d, 1H, J=8.8 Hz), 7.95 (s, 1H), 7.6-7.52 (m, 2H), 7.48-7.34 (m, 3H), 7 (dd, 1H, J=8.8, 2 Hz), 6.87 (d, 1H, J=2 Hz), 4.21 (t, 2H, J=5.6 Hz), 3.65 (t, 2H, J=5.6 Hz), 2.89 (t, 2H, J=5.6 Hz), 2.78-2.52 (m, 8H), 2.6 (t, 2H, J=5.6 Hz); $^{13}$C NMR (100 MHz, DMSO-d$_6$) δ 174.4, 163, 157.5, 154.2, 132, 128.9, 128.1, 127.8, 126.9, 123.8, 117.6, 115.2, 101.2, 66.5, 60.2, 58.4, 56.4, 53.2, 53; $^{13}$C NMR (100 MHz, CDCl$_3$) δ 175.7, 163.2, 158, 152.8, 132.1, 129.1, 128.6, 128.3, 128, 125.5, 118.7, 115, 101, 66.8, 59.4, 57.8, 56.9, 53.7, 52.9. HRMS (ESI) Calcd for C$_{23}$H$_{27}$O$_4$N$_2$: 395.1965 (M+H)*. Found 395.1957. Anal. Calcd. for C$_{23}$H$_{26}$N$_2$O$_4$: C, 70.03; H, 6.64; N, 7.10. Found: C, 69.79; H, 6.65; N, 7.07.

7-[2-[4-(2-Hydroxyethyl)piperazin-1-yl]ethoxy]-3-(4-methoxyphenyl) chromen-4-one (8b)

Yield: 73%; mp 145-146° C.; $^1$H NMR (400 MHz, CDCl$_3$) δ 8.2 (d, 1H, J=8.8 Hz), 7.92 (s, 1H), 7.5 (d, 2H, J=9.2 Hz), 7 (dd, 1H, J=8.8, 2.4 Hz), 6.97 (d, 2H, J=9.2 Hz), 6.86 (d, 1H, J=2.4 Hz), 4.2 (t, 2H, J=5.8 Hz), 3.84 (s, 3H), 3.63 (t, 2H, J=5.2 Hz), 2.88 (t, 2H, J=5.8 Hz), 2.74-2.54 (m, 8H), 2.57 (t, 2H, J=5.2 Hz); $^{13}$C NMR (100 MHz, CDCl$_3$) δ 176, 163.1, 159.7, 158, 152.2, 130.2, 127.9, 125, 124.3, 118.6, 114.9, 114.1, 100.9, 66.7, 59.5, 57.7, 56.9, 55.5, 53.5, 52.9. HRMS (ESI) Calcd for C$_{24}$H$_{29}$O$_5$N$_2$: 425.2071 (M+H)$^+$. Found 425.2071. Anal. Calcd. for C$_{24}$H$_{28}$N$_2$O$_5$: C, 67.91; H, 6.65; N, 6.60. Found: C, 68.15; H, 6.71; N, 6.56.

3-(4-Chlorophenyl)-7-(2-(4-(2-hydroxyethyl)piperazin-1-yl)ethoxy)-4H-chromen-one (8c)

Yield: 74%; mp 152-153° C.; $^1$H NMR (400 MHz, CDCl$_3$) δ 8.2 (d, 1H, J=8.8 Hz), 7.94 (s, 1H), 7.51 (d, 2H, J=8.2 Hz), 7.41 (d, 2H, J=8.2 Hz), 7.02 (dd, 1H, J=8.8, 2.4 Hz), 6.87 (d, 1H, J=2.4 Hz), 4.21 (t, 2H, J=5.6 Hz), 3.62 (t, 2H, J=5.2 Hz), 2.88 (t, 2H, J=5.6 Hz), 2.72-2.5 (m, 8H), 2.57 (t, 2H, J=5.2 Hz); $^{13}$C NMR (100 MHz, CDCl$_3$) δ 175.5, 163.4, 158, 152.7, 134.3, 130.5, 130.4, 128.8, 127.9, 124.4, 118.5, 115.2, 101, 66.8, 59.3, 57.8, 56.9, 53.8, 52.9. HRMS (ESI) Calcd for $C_{23}H_{26}O_4N_2Cl$: 429.1576 (M+H)$^+$. Found 429.1577. Anal. Calcd. for $C_{23}H_{25}N_2O_4Cl$: C, 64.41; H, 5.88; N, 6.53. Found: C, 64.52; H, 6.01; N, 6.50.

General Procedure for the Synthesis of Cytisinyl-Linked Isoflavones 10.

A mixture of 0.5 mmol of 7-(2-bromoethoxy)isoflavone 6, cytisine (143 mg, 0.75 mmol), NaI (75 mg, 0.5 mmol), and diisopropylethylamine (0.3 mL, 3.5 mmol) in DMF (5 mL) was stirred for 2-4 h at 80° C. under a nitrogen atmosphere. The mixture was cooled and poured into cold water. A precipitate was collected and purified by column chromatography using methanol-dichloromethane (2:98 to 5:95) to afford cytisinyl-linked isoflavones 10 as white solids.

(1R,5S)-3-(2-((4-Oxo-3-phenyl-4H-chromen-7-yl) oxy)ethyl)-3,4,5,6-tetrahydro-1H-1,5-methanopyrido [1,2-a][1,5]diazocin-8(2H)-one (10a)

Yield: 72%; mp 197-198° C. (lit[13] mp 195-196° C.); $^1$H NMR (400 MHz, DMSO-d$_6$) δ 8.46 (s, 1H), 7.99 (d, 1H, J=9 Hz), 7.62-7.55 (m, 2H), 7.48-7.34 (m, 3H), 7.29 (dd, 1H, J=8.9, 6.7 Hz), 7.11 (d, 1H, J=2.4 Hz), 6.98 (dd, 1H, J=9, 2.4 Hz), 6.18 (dd, 1H, J=8.9, 1.2 Hz), 6.07 (dd, 1H, J=6.7, 1.2 Hz), 4.2-4.04 (m, 2H), 3.82-3.64 (m, 2H), 3.06-2.98 (m, 2H), 2.94-2.86 (m, 1H), 2.76-2.62 (m, 2H), 2.52-2.34 (m, 3H), 1.79 (d, 1H, J=12.5 Hz), 1.7 (d, 1H, J=12.5 Hz); $^{13}$C NMR (100 MHz, DMSO-d$_6$) δ 174.4, 162.9, 162.2, 157.4, 154.2, 152.1, 138.7, 132, 128.9, 128.2, 127.8, 126.9, 123.7, 117.6, 115.3, 115.1, 103.7, 101.3, 66.3, 60.3, 59.4, 55.7. 49.5, 34.6, 27.3, 25. NMR data was consistent with reported data in DMSO-d$_6$.

(1R,5S)-3-(2-((3-(4-Methoxyphenyl)-4-oxo-4H-chromen-7-yl)oxy)ethyl)-3,4,5,6-tetrahydro-1H-1,5-methanopyrido[1,2-a][1,5]diazocin-8(2H)-one (10b)

Yield: 76%; mp 117-118° C. (lit[13] mp 85-86° C.); $^1$H NMR (400 MHz, DMSO-d$_6$) 8.41 (s, 1H), 7.98 (d, 1H, J=8.8 Hz), 7.52 (d, 2H, J=8.8 Hz), 7.29 (dd, 1H, J=8.9, 6.9 Hz), 7.09 (d, 1H, J=2 Hz), 7.04-6.92 (m, 3H), 6.18 (dd, 1H, J=8.9, 0.8 Hz), 6.06 (d, 1H, J=6.9 Hz), 4.18-4.04 (m, 2H), 3.82-3.66 (m, 2H), 3.79 (s, 3H), 3.06-2.98 (m, 2H), 2.94-2.86 (m, 1H), 2.76-2.62 (m, 2H), 2.52-2.32 (m, 3H), 1.84-1.66 (m, 2H); $^{13}$C NMR (100 MHz, CDCl$_3$) δ 175.9, 163.7, 162.9, 159.6, 157.9, 152.2, 151.4, 138.7, 130.2, 127.8, 124.8, 124.3, 118.5, 116.7, 114.8, 114, 104.6, 100.8, 66.7, 60.9, 60.4, 56.2, 55.4, 50, 35.6, 28.1, 25.7. NMR data was consistent with reported data in DMSO-d$_6$[13]. HRMS (ESI) Calcd for $C_{29}H_{29}O_5N_2$: 485.2071 (M+H)$^+$. Found: 485.2071. Anal. Calcd. for $C_{29}H_{25}N_2O_5$: C, 71.88; H, 5.82; N, 5.78. Found: C, 71.60; H, 5.75; N, 5.73.

(1 S,5S)-3-(2-((3-(4-chlorophenyl)-4-oxo-4H-chromen-7-yl)oxy)ethyl)-3,4,5,6-tetrahydro-1H-1,5-methanopyrido[1,2-a][1,5]diazocin-8(2H)-one (10c)

Yield: 76%; mp 146-147° C.; $^1$H NMR (400 MHz, CDCl$_3$) δ 8.16 (d, 1H, J=8.8 Hz), 7.94 (s, 1H), 7.51 (d, 2H, J=8.6 Hz), 7.4 (d, 2H, J=8.6 Hz), 7.3-7.18 (m, 1H), 6.9 (dd, 1H, J=8.8, 2 Hz), 6.76 (d, 1H, J=2 Hz), 6.43 (d, 1H, J=8.8 Hz), 5.96 (d, 1H, J=6.8 Hz), 4.14-3.86 (m, 4H), 3.08-2.92 (m, 3H), 2.75 (t, 2H, J=5.6 Hz), 2.6-2.42 (m, 3H), 1.94-1.76 (m, 2H); $^{13}$C NMR (100 MHz, CDCl$_3$) δ 175.5, 163.7, 163.1, 158, 152.7, 151.4, 138.8, 134.2, 130.5, 130.3, 128.8, 127.9, 124.3, 118.4, 116.8, 115.1, 104.7, 100.9, 66.8, 61, 60.5, 56.2, 50.1, 35.6, 28.1, 25.8. HRMS (ESI) Calcd for $C_{28}H_{26}O_4N_2C$: 489.1576 (M+H)$^+$. Found: 489.1577. Anal. Calcd. for $C_{28}H_{25}ClN_2O_4$: C, 68.78; H, 5.15; N, 5.73. Found: C, 69.02; H, 5.41; N, 5.63.

(1R,5S)-3-(2-((3-(4-Chlorophenyl)-2-methyl-4-oxo-4H-chromen-7-yl)oxy)ethyl)-3,4,5,6-tetrahydro-1H-1,5-methanopyrido[1,2-a][1,5]diazocin-8(2H)-one (10d)

Yield: 62%; mp 186-187° C.; $^1$H NMR (400 MHz, methanol-d$_4$) δ 7.96 (d, 1H, J=8.4 Hz), 7.45 (d, 2H, J=8.6 Hz), 7.39 (dd, 1H, J=8.9, 6.9 Hz), 7.28 (d, 2H, J=8.6 Hz), 6.94-6.9 (m, 1H), 6.89 (d, 1H, J=2 Hz), 6.35 (dd, 1H, J=8.9, 1.2 Hz), 6.25 (dd, 1H, J=6.9, 1.2 Hz), 4.12-4.04 (m, 2H), 4 (d, 1H, J=15.4 Hz), 3.88 (dd, 1H, J=15.4, 6.4 Hz), 3.13-2.98 (m, 3H), 2.78-2.72 (m, 2H), 2.6-2.44 (m, 3H), 2.3 (s, 3H), 1.96-1.82 (m, 2H); $^{13}$C NMR (100 MHz, methanol-d$_4$) δ 178, 165.8, 165.5, 165.1, 159.2, 153.8, 141.2, 134.9, 133.6, 133.2, 129.6, 128, 123.2, 117.8, 116.4, 116.2, 107.7, 101.9, 67.8, 61.9, 61.4, 57.3, 51.6, 36.9, 29.5, 26.3, 19.6. HRMS (ESI) Calcd for $C_{29}H_{28}ClN_2O_4$: 503.1732 (M+H)$^+$. Found: 503.1735. Anal. Calcd. for $C_{29}H_{27}O_4N_2Cl$: C, 69.25; H, 5.41; N, 5.57. Found: C, 68.98; H, 5.36; N, 5.50.

3-(4-Chlorophenyl)-7-(hex-5-en-1-yloxy)-2-methyl-4H-chromen-4-one (11d)

To a solution of 7-hydroxyflavone 3d (573 mg, 2 mmol) in DMF (10 mL) was added $K_2CO_3$ (690 mg, 5 mmol) and 6-bromo-1-hexene (0.6 mL, 4.5 mmol). The mixture was stirred at 80° C. for 1 h under a nitrogen atmosphere. The mixture was cooled, diluted with water, and extracted with ethyl acetate. The combined organic layers were washed successively with water and brine and dried over anhydrous MgSO$_4$. The product was isolated by column chromatography using ethyl acetate-hexanes as eluent (from 5:95 to 1:5) to afford 600 mg (81%) of 11d as a white solid: mp 104° C.; $^1$H NMR (400 MHz, DMSO-d$_6$) δ 7.93 (d, 1H, J=8.6 Hz), 7.49 (d, 2H, J=8.4 Hz), 7.32 (d, 2H, J=8.4 Hz), 7.14 (d, 1H, J=2.3 Hz), 7.04 (dd, 1H, J=8.6; 2.3 Hz), 5.9-5.76 (m, 1H), 5.08-4.95 (m, 2H), 4.13 (t, 2H, J=6.4 Hz), 2.27 (s, 3H), 2.14-2.07 (m, 2H), 1.82-1.72 (m, 2H), 1.58-1.48 (m, 2H); $^{13}$C NMR (100 MHz, DMSO-d$_6$) δ 174.6, 163.1 (163.13), 163.1 (163.11), 157.1, 138.5, 132.5, 132.3, 132.1, 128.1, 126.8, 121.3, 116.3, 115, 114.9, 100.8, 68.3, 32.8, 27.9, 24.6, 19.2. HRMS (ESI) m/z Calcd for $C_{22}H_{22}O_3Cl$: 369.1263 (M+H)$^+$. Found: 369.1253. Anal. Calcd. for $C_{22}H_{22}O_3Cl$: C, 71.64; H, 5.74. Found: C, 71.55; H, 5.59.

3-(4-Chlorophenyl)-2-methyl-7-(4-(oxiran-2-yl)butoxy)-4H-chromen-4-one (12d)

A solution of 77% meta-chloroperoxybenzoic acid (896 mg, 4 mmol) in dichloromethane (5 mL) was added to a solution of 11d (338 mg, 0.92 mmol) in dichloromethane (5 mL). The mixture was stirred for 4 h at 25° C. under a nitrogen atmosphere. The product was poured into saturated NaHCO$_3$ solution and extracted with dichloromethane. The organic layers were washed with brine and dried over anhydrous MgSO$_4$. The product was purified by column chromatography using methanol-dichloromethane (ratio ranging from 2:98 to 2:48) to afford 234 mg (76%) of 12d: mp 118-119° C.; $^1$H NMR (400 MHz, CDCl$_3$) δ 8.11 (d, 1H, J=8.8 Hz), 7.4 (d, 2H, J=8.4 Hz), 7.23 (d, 2H, J=8.4 Hz), 6.95 (dd, 1H, J=8.8, 2.4 Hz), 6.82 (d, 1H, J=2.4 Hz), 4.08 (t, 2H, J=6.2 Hz), 3-2.92 (m, 1H), 2.79 (t, 1H, J=4.4 Hz), 2.54-2.48 (m, 1H), 2.29 (s, 3H), 1.96-1.86 (m, 2H), 1.76-

1.54 (m, 4H); $^{13}$C NMR (100 MHz, CDCl$_3$) δ 176.1, 163.5, 162.8, 157.7, 133.8, 132, 131.8, 128.7, 127.7, 122.4, 117.2, 114.7, 100.5, 68.4, 52.2, 47.1, 32.3, 28.9, 22.8, 19.5. HRMS (ESI) Calcd for C$_{22}$H$_{20}$O$_4$Cl: 385.1201 (M+H)$^+$. Found: 385.1212. Anal. Calcd. for C$_{22}$H$_{21}$ClO$_4$: C, 68.66; H, 5.50. Found: C, 68.39; H, 5.50.

(1S,5S)-3-(6-((3-(4-Chlorophenyl)-2-methyl-4-oxo-4H-chromen-7-yl)oxy)-2-hydroxyhexyl)-3,4,5,6-tetrahydro-1H-1,5-methanopyrido[1,2-a][1,5]diazocin-8(2H)-one (13d)

A mixture of 12d (327 mg, 0.8 mmol) and cytisine (194 mg, 1 mmol) in absolute ethanol (9 mL) was stirred in a pressure tube for 20 h at 90° C. The solvent was evaporated, and the product was purified by column chromatography using methanol-dichloromethane (2:48) to afford 470 mg (96%) of 13d as a mixture of diastereoisomers: $^1$H NMR (400 MHz, CDCl$_3$) δ 8.08 and 8.07 (two d, 1H, J=9.2 Hz), 7.39 (d, 2H, J=8.4 Hz), 7.32-7.16 (m, 3H), 6.96-6.86 (m, 1H), 6.82-6.76 (m, 1H), 6.46-6.38 (m, 1H), 6.04-5.94 (m, 1H), 4.18-3.84 (m, 3H), 3.64-3.5 (m, 1H), 3.12-2.82 (m, 3H), 2.7-2.62 (m, 1H), 2.56-2.24 (m, 4H), 2.27 (two s, 3H), 2.2-2.1 (m, 1H), 1.98-1.74 (m, 4H), 1.66-1.3 (m, 4H); $^{13}$C NMR (100 MHz, DMSO-d$_6$) δ 174.6, 163.2 (163.18), 163.2 (163.17), 163.1, 162.2, 157.1, 152.2 (152.23), 152.2 (152.21), 138.7, 138.6, 132.5, 132.3, 132.1, 128.1, 126.7, 121.3, 116.3, 115.1, 114.9, 103.7, 103.6, 100.8, 68.5, 67.1, 66.9, 63.05, 62.98, 61.4, 60.8, 60.4, 60, 49.7, 34.8, 34.7, 34.4, 28.64, 28.58, 27.6, 27.4, 25.2, 21.23, 21.15, 19.2. HRMS (ESI) Calcd for C$_{33}$H$_{36}$O$_5$N$_2$Cl: 575.2318 (M+H)$^+$. Found: 575.2312. Anal. Calcd. for C$_{33}$H$_{35}$O$_5$N$_2$Cl·½H$_2$O: C, 67.86; H, 6.21; N, 4.80. Found: C, 68.26; H, 6.41; N, 4.72.

(1S,5S)-3-(6-((3-(4-Chlorophenyl)-2-methyl-4-oxo-4H-chromen-7-yl)oxy)-2-oxohexyl)-3,4,5,6-tetrahydro-1H-1,5-methanopyrido[1,2-a][1,5]diazocin-8(2H)-one (14d)

To a suspension of Dess-Martin periodinane (520 mg, 1.2 mmol) in dichloromethane (8 mL) was added a solution of 13d (470 mg, 0.8 mmol) in dichloromethane (5 mL). The mixture was stirred at 25° C. for 2 h, diluted with dichloromethane, and washed with a 3:2 saturated solution of Na$_2$S$_2$O$_3$ and NaHCO$_3$ (20 mL. The combined organic layers were washed with brine and dried over anhydrous MgSO$_4$. The product was purified by column chromatography using methanol-dichloromethane (1:98) to afford 380 mg (81%) of 14d as a white foam: $^1$H NMR (400 MHz, CDCl$_3$) δ 8.1 (d, 1H, J=8.8 Hz), 7.4 (d, 2H, J=7.9 Hz), 7.32-7.2 (m, 1H), 7.23 (d, 2H, J=7.9 Hz), 6.92 (d, 1H, J=8.8 Hz), 6.84-6.78 (m, 1H), 6.47 (d, 1H, J=8.8 Hz), 6 (d, 1H, J=6.8 Hz), 4.19 (d, 1H, J=15.6 Hz), 3.97 (t, 2H, J=5.2 Hz), 3.9 (dd, 1H, J=15.6, 6.8 Hz), 3.2-2.86 (m, 4H), 2.74 (d, 1H, J=10.4 Hz), 2.62 (d, 1H, J=10.8 Hz), 2.55 (d, 1H, J=10.8 Hz), 2.52-2.42 (m, 1H), 2.29 (s, 3H), 2.3-2.22 (m, 1H), 2.18-2.06 (m, 1H), 1.95 (d, 1H, J=12.7 Hz), 1.82 (d, 1H, J=12.7 Hz), 1.7-1.52 (m, 4H); $^{13}$C NMR (100 MHz, CDCl$_3$) δ 210.5, 176.1, 163.6, 163.5, 162.9, 157.7, 151.2, 138.8, 133.8, 132, 131.8, 128.7, 127.6, 122.4, 117.1, 116.9, 114.7, 104.8, 100.5, 68.2, 67.6, 60.8 (60.83), 60.8 (60.76), 50.1, 39.1, 35.4, 28.5, 28.2, 25.4, 19.9, 19.5. HRMS (ESI) Calcd for C$_{33}$H$_{34}$O$_5$N$_2$Cl: 573.2151 (M+H)$^+$. Found: 573.2156. Anal. Calcd. for C$_{33}$H$_{23}$O$_5$N$_2$Cl·½H$_2$O: C, 68.09; H, 5.89; N, 4.81. Found: C, 68.02; H, 5.95; N, 4.71.

N-(22-((3-(4-chlorophenyl)-2-methyl-4-oxo-4H-chromen-7-yl)oxy)-15-oxo-18-(((1S,5S)-8-oxo-1,5,6,8-tetrahydro-2H-1,5-methanopyrido[1,2-a][,5]diazocin-3(4H)-yl)methyl)-3,6,9,12-tetraoxa-16,17-diazadocos-17-en-1-yl)-5-((4S)-2-oxohexahydro-1H-thieno[3,4-d]imidazol-4-yl)pentanamide (15d)

A mixture of hydrazide-PEG$_4$-biotin (Thermo Fisher, 50 mg, 0.1 mmol), 14d (57 mg, 0.1 mmol), and cerium trichloride (3 mg, 0.01 mmol) in methanol (3 mL) was stirred at 60° C. for 4 h. The solvent was evaporated, and the product was isolated by preparative chromatography using methanol-dichloromethane (8:92) to afford 25 mg (24%) of 15d as a mixture of syn/anti-isomers: $^1$H NMR (400 MHz, CDCl$_3$) δ 10.51 and 10.3 (two s, 1H), 7.98 (d, 1H, J=8.7 Hz), 7.45 (d, 2H, J=8.3 Hz), 7.36-7.22 (m, 1H), 7.28 (d, 2H, J=8.3 Hz), 7.02-6.93 (m, 2H), 6.8-6.64 (m, 1H), 6.28 and 6.24 (two d, 1H, J=9 Hz), 6.07 and 6.02 (two d, 1H, J=6.8 Hz), 5.48-5.36 (m, 1H), 5.18-5.08 (m, 1H), 4.3-4.36 (m, 1H), 4.24-4.18 (m, 1H), 4.16-4.08 (m, 2H), 3.9-3.8 (m, 2H), 3.78-3.4 (m, 16H), 3.38-3.2 (m, 2H), 3.18-3.08 (m, 3H), 3.06-2.6 (m, 6H), 2.54-2.02 (7H), 2-1.46 (m, 10H), 1.44-1.22 (m, 4H). MS (ESI): 1060 (M+H)$^+$, 1077 (M+NH$_4$)+, 1082 (M+Na)$^+$, 1098 (M+K)$^+$. HRMS (ESI) Calcd for C$_{54}$H$_{71}$O$_{11}$N$_7$ClS: 1060.4615 (M+H)+. Found: 1060.4612.

(1S,5S)-3-(2-Hydroxy-6-phenoxyhexyl)-3,4,5,6-tetrahydro-1H-1,5-methanopyrido[1,2-a][1,5]diazocin-8(2H)-one (16)

A mixture of phenol (2 g, 21.3 mmol), K$_2$CO$_3$ (8.8 g, 63.4 mmol), and 6-bromo-1-hexene (3.4 mL, 25.5 mmol) in DMF (15 mL) was stirred at 60° C. for 5 h under a nitrogen atmosphere. The mixture was cooled, poured into water, and extracted with dichloromethane. The combined organic layers were washed successively with water and brine and dried over anhydrous MgSO$_4$. The product was purified by column chromatography using ethyl acetate-hexanes (5:95) to afford 1.8 g (96%) of (hex-5-en-1-yloxy)benzene as colorless oil: $^1$H NMR (400 MHz, CDCl$_3$) δ 7.32-7.24 (m, 2H), 6.96-6.86 (m, 3H), 5.9-5.76 (m, 1H), 5.08-4.94 (m, 2H), 3.96 (t, 2H, J=6.5 Hz), 2.18-2.08 (m, 2H), 1.84-1.76 (m, 2H), 1.62-1.52 (m, 2H); $^{13}$C NMR (100 MHz, CDCl$_3$) δ 159.2, 138.7, 129.6, 120.6, 114.9, 114.6, 67.7, 33.6, 28.9, 25.5. NMR data was consistent with reported data in CDCl$_3$. A mixture of 77% meta-chloroperbenzoic acid (3.4 g, 15.3 mmol) in dichloromethane (3 mL) was added dropwise to a solution of (hex-5-en-1-yloxy)benzene (1.8 g, 10.2 mmol) in dichloromethane (3 mL). The mixture was stirred at 25° C. for 2 h. The mixture was poured into saturated solution of NaHCO$_3$ and extracted with dichloromethane. The combined organic layers were washed with brine, and dried over anhydrous MgSO$_4$. The product was purified by column chromatography using ethyl acetate-hexanes (5:95) to afford 1.6 g (81%) of 2-(4-phenoxybutyl)oxirane as colorless oil: $^1$H NMR (400 MHz, CDCl$_3$) δ 7.32-7.24 (m, 2H), 6.96-6.86 (m, 3H), 3.98 (t, 2H, J=6.3 Hz), 2.98-2.9 (m, 1H), 2.78-2.72 (m, 1H), 2.52-2.46 (m, 1H), 1.9-1.8 (m, 2H), 1.72-1.58 (m, 4H); $^{13}$C NMR (100 MHz, CDCl$_3$) δ 159.1, 129.6, 120.7, 114.6, 67.6, 52.3, 47.2, 32.3, 29.2, 22.8. NMR data was consistent with reported data in CDCl$_3$. A mixture of 2-(4-phenoxybutyl)oxirane (385 mg, 2 mmol) and cytisine (457 mg, 2.4 mmol) in methanol (8 mL) was stirred in a pressure tube for 8 h at 90° C. The solvent was evaporated, and the product was purified by column chromatography using methanol-dichloromethane (ratio ranging from 2:98 to 7:93) to afford 750 mg (98%) of 16 as a mixture of diastereoisomers: ¹H NMR (400 MHz, CDCl₃) δ 7.32-7.22 (m, 3H), 6.92 (t, 1H, J=7.3 Hz), 6.89-6.84 (m, 2H), 6.44-6.4 (m, 1H), 6.01-5.94 (m, 1H), 4.11 and 4.05 (two d, 1H, J=15.5 Hz), 3.96-3.84 (m, 3H), 3.62-3.46 (m, 1H), 3.09-2.95 (m, 2H), 2.88 and 2.83 (two d, 1H, J=11.1 and 10.7 Hz), 2.66-2.4 (m, 3H), 2.36-2.06 (m, 3H), 1.97-1.67 (m, 4H), 1.64-1.22 (m, 4H); ¹³C NMR (100 MHz, CDCl₃) δ 163.4 (163.44), 163.4 (163.42), 159.1, 150.9, 150.6, 138.9, 138.8, 129.5, 120.55, 120.53, 117.03, 116.96, 114.52, 114.5, 104.8, 104.7, 67.64, 67.63, 66.5, 65.9, 63.9, 63.5, 62.7, 62, 59.1, 58.9, 50.1, 50, 35.8, 35.2, 34.5, 34.2, 29.4, 29.3, 28.3, 27.9, 26, 25.9, 22.2, 22.1. HRMS (ESI) Calcd for C₂₃H₃₁O₃N₂: 383.2329 (M+H)+. Found: 383.2340. Anal. Calcd. for C₃₃H₂₀N₂O₃: C, 72.22; H, 7.91; N, 7.32. Found: C, 71.94; H, 7.93; N, 7.28.

(1S,5S)-3-(2-oxo-6-phenoxyhexyl)-3,4,5,6-tetra-hydro-1H-1,5-methanopyrido[1,2-a][1,5]diazocin-8 (2H)-one (17)

To a suspension of Dess-Martin periodinane (424 mg, 1 mmol) in dichloromethane (3 mL) was added a solution of 16 (258 mg, 0.7 mmol) in dichloromethane (3 mL). The mixture was stirred at 25° C. for 2 h, and the reaction was quenched with a 2:1 mixture of saturated Na₂S2O₃ and NaHCO₃ (10 mL). The product was extracted with dichloromethane. The combined organic layers were washed successively with saturated NaHCO₃ solution and brine and dried over anhydrous MgSO₄. The solvent was evaporated, and the product was purified by column chromatography using methanol-dichloromethane (1:24) to afford 147 mg (57%) of 17 as a colorless, viscous oil: ¹H NMR (400 MHz, CDCl₃) δ 7.32-7.2 (m, 3H), 6.93 (t, 1H, J=7.3 Hz), 6.9-6.84 (m, 2H), 6.45 (d, 1H, J=9 Hz), 5.98 (d, 1H, J=6.8 Hz), 4.17 (d, 1H, J=15.5 Hz), 3.94-3.82 (m, 3H), 3.08-2.84 (m, 4H), 2.72 (d, 1H, J=10.6 Hz), 2.62 (d, 1H, J=10.9 Hz), 2.58-2.51 (m, 1H), 2.5-2.42 (m, 1H), 2.3-2.04 (m, 2H), 1.93 (d, 1H, J=12.8 Hz), 1.8 (d, 1H, J=12.8 Hz), 1.66-1.5 (m, 4H); ¹³C NMR (100 MHz, CDCl₃) δ 210.6, 163.6, 159.1, 151.1, 138.8, 129.5, 120.7, 116.9, 114.6, 104.8, 67.6, 67.4, 60.7 (60.73), 60.7 (60.7), 50.1, 39.3, 35.5, 28.8, 28.2, 25.5, 20. HRMS (ESI) Calcd for C₂₃H₂₉O₃N₂: 381.2173 (M+H)⁺. Found 381.2177. Removing traces of solvent from the viscous oil precluded obtaining a satisfactory combustion analysis of 17. An oxime derivative of 17 was prepared using 110 mg of 17, hydroxylamine hydrochloride (30 mg, 0.4 mmole), and sodium acetate (39 mg, 0.5 mmol) in ethanol to afford 83 mg (72%) of a hygroscopic solid as mixture of syn/anti-isomers: mp 62-70° C. (recrystallized from diethyl ether-hexanes). Anal. Calcd. for C₂₃H₂₉N₃O₃.H₂O: C, 66.81; H, 7.56; N, 10.16. Found: C, 66.93; H, 7.28; N, 10.07.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A method of treating prostate or colorectal cancer, the method comprising administering to a patient in need of prostate or colorectal cancer treatment an effective amount of a cytisine-linked isoflavonoid compound represented by formula (I):

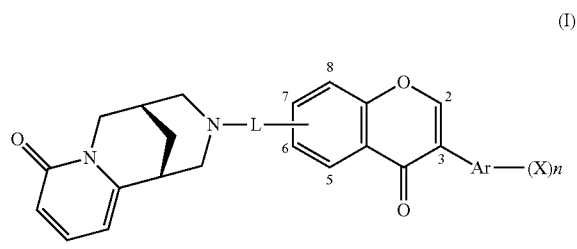

or pharmaceutically acceptable salt thereof or a pharmaceutical composition thereof,
wherein Ar is an aryl or heteroaryl; n is an integer from 1 to 5; each X is independently a halide, or alkoxy, or more than one X on Ar together form a cyclic ether structure; and wherein the compound is substituted on the C-2 position with H, alkyl, cycloalkyl or alkoxy, substituted on the C-5, C-6, C-7, and C-8 positions independently with H, hydroxy (OH), alkyl, cycloalkyl, alkoxy, L is a substituted or unsubstituted di-radical linker group that links the cytisinyl group to either the C-5, C-6, C-7 or C-8 position.

2. The method of claim 1, wherein the compound is represented by of formula (II):

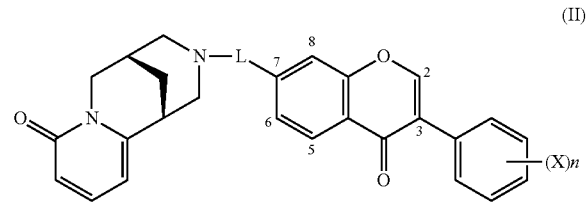

or pharmaceutically acceptable salt thereof or a pharmaceutical composition thereof.

3. The method of claim 1, wherein Ar is a heteroaryl.

4. The method of claim 3, wherein Ar is pyridinyl, diazinyl, pyrimidinyl, oxazolyl or imidazolyl.

5. The method of claim 1, wherein the C-2 substituent is hydrogen H or methyl; n is 1 or 2, X is a halide or an alkoxy group or two X together form a cyclic ether structure; the C-5 substituent is H, hydroxy or alkoxy; the C-6 substituent is hydrogen H; the C-8 substituent is H, alkyl or substituted alkyl.

6. The method of claim 2, wherein the C-2 substituent is hydrogen H or methyl; n is 1 or 2, X is a halide or an alkoxy group or two X together form a cyclic ether structure; the C-5 substituent is H, hydroxy or alkoxy; the C-6 substituent is hydrogen H; the C-8 substituent is H, methyl, alkyl or substituted alkyl.

7. The method of claim 1, wherein L is a diradical —R₂—, —R₂Z—(R'₂)ₘ—, or —R₂Z(R'₂)ₘO—, where m is 0 or 1; R₂ and R'₂ are independently a C₁₋₈ diradical alkyl, and Z represents either (CH₂)ₙ₂, —CH(OH)—, —CO—, —C(O)O—, —OC(O)—, or —O—, wherein n2 is 1-4.

8. The method of claim 2, wherein L is a diradical —R₂—, —R₂Z—(R'₂)ₘ—, or —R₂Z(R'₂)ₘO—, where m is 0 or 1; R₂ and R'₂ are independently a C₁₋₈ diradical alkyl, and Z represents either —$(CH_2)_{n2}$—, —CH(OH)—, —CO—, —C(O)O—, —OC(O)—, or —O—, wherein n2 is 1-4.

* * * * *

UNITED STATES PATENT AND TRADEMARK OFFICE
CERTIFICATE OF CORRECTION

PATENT NO. : 10,188,743 B2
APPLICATION NO. : 15/714647
DATED : January 29, 2019
INVENTOR(S) : Liu et al.

Page 1 of 1

It is certified that error appears in the above-identified patent and that said Letters Patent is hereby corrected as shown below:

In the Specification

Column 1, Lines 13-19, should read:
STATEMENT REGARDING FEDERALLY SPONSORED RESEARCH
This invention was made with government support under Contract Nos. R21 CA139359 and R01 CA172379 awarded by the National Institutes of Health and Grant No. W81XWH-16-1-0635 awarded by the Department of Defense. The government has certain rights in the invention.

Signed and Sealed this
Eleventh Day of January, 2022

Drew Hirshfeld
*Performing the Functions and Duties of the
Under Secretary of Commerce for Intellectual Property and
Director of the United States Patent and Trademark Office*